United States Patent [19]

Badger et al.

[11] Patent Number: 4,963,557
[45] Date of Patent: Oct. 16, 1990

[54] IMMUNOMODULATORY AZASPIRANES

[75] Inventors: Alison M. Badger, Bryn Mawr; Elaine N. Cheeseman, Phoenixville; Michael J. DiMartino, Philadelphia; James W. Dorman, West Chester; Christopher K. Mirabelli, Exton; Donald H. Picker, Merion; David A. Schwartz, Exton, all of Pa.

[73] Assignee: SmithKline Beecham Corporation, Philadelphia, Pa.

[21] Appl. No.: 244,229

[22] Filed: Sep. 13, 1988

Related U.S. Application Data

[63] Continuation-in-part of Ser. No. 101,704, Sep. 28, 1987, abandoned.

[51] Int. Cl.$^5$ .......................................... C07D 213/00
[52] U.S. Cl. .................................... 514/278; 514/409; 546/16; 548/408
[58] Field of Search ................... 546/16; 514/278, 409; 548/408

[56] References Cited

U.S. PATENT DOCUMENTS

| | | | |
|---|---|---|---|
| 3,106,552 | 10/1963 | Grogaw | 546/16 |
| 3,256,277 | 6/1966 | Rice et al. | |
| 3,282,947 | 11/1966 | Rice et al. | |
| 3,326,925 | 6/1967 | Giudicelli et al. | 546/16 |
| 3,418,324 | 12/1968 | Rice et al. | 546/16 |
| 3,424,755 | 1/1969 | Denss | 548/408 |
| 3,733,412 | 5/1973 | deBock | 514/409 |
| 3,825,546 | 7/1974 | Rice et al. | |
| 3,907,801 | 9/1975 | Uri | 546/16 |
| 4,468,393 | 8/1984 | Geschickter et al. | |
| 4,654,333 | 3/1987 | Tenoso et al. | |

FOREIGN PATENT DOCUMENTS

| | | | |
|---|---|---|---|
| 186505A2 | 7/1986 | European Pat. Off. | |
| WO85/05031 | 11/1985 | PCT Int'l Appl. | |
| 823338 | 11/1959 | United Kingdom | 546/16 |
| 929739 | 6/1963 | United Kingdom | |

OTHER PUBLICATIONS

Rice et al., J. Heterocycl. Chem., 10 (5), 737–735, 741 (1973).
Rice et al., J. Med. Chem., 6, 388–402 (1963).
Rice et al., J. Heterocycl. Chem., 1(3), 125–127 (1964).
DiMartino et al., J. Pharmacol. Exp. Therapeut., 236, 103–110 (1986).
Badger et al., Immunopharmacol., 10, 201–207 (1985).

*Primary Examiner*—Donald G. Daus
*Attorney, Agent, or Firm*—Carol G. Canter; Stuart R. Suter; Edward T. Lentz

[57] ABSTRACT

A pharmaceutical composition comprising a pharmaceutically acceptable carrier or diluent and an effective amount of an azaspirane derivative, a method of treating an animal in need of immunomodulation which comprises administering to such animal an effective amount of an azaspirane derivative, and certain azaspirane derivatives.

39 Claims, No Drawings

IMMUNOMODULATORY AZASPIRANES

CROSS REFERENCE TO RELATED APPLICATIONS

This application is a continuation-in-part application of Ser. No. 101,704, filed Sept. 28, 1987, now abandoned.

BACKGROUND OF THE INVENTION

This invention relates to a non metal containing spirogermanium analog, a pharmaceutical composition containing such an analog and a pharmaceutically acceptable carrier or diluent, and a method of treating rheumatoid arthritis in an animal in need thereof which comprises administering an effective amount of such an analog to such animal.

Geschickter et al., U.S. Pat. No. 4,468,393, issued Aug. 28, 1984, claims a method of treating arthritis using various germanium containing spirogermanium analogs including:

N (3-dimethylaminopropyl) 2-aza 8,8 dimethyl-8-germanspiro [4,5]decane;

N (3 dimethylaminopropyl) 2-aza-8,8 diethyl 8-germanspiro [4,5]decane;

N-(3 dimethylaminopropyl) 2 aza 8,8 dipropyl 8-germanspiro [4,5]decane; and

N (3 dimethylaminopropyl) 2 aza 8,8 dibutyl-8-germanspiro [4,5]decane.

Tenoso et al., U.S. Pat. No. 4,654,333, issued Mar. 31, 1987, claims a method for treating multiple sclerosis, which comprises administering to a patient suffering from the same a multiple sclerosis treatment effective amount of a spirogermanium selected from the group consisting of:

N (3 dimethylaminopropyl) 2-aza 8,8 dimethyl 8-germanspiro [4:5]decane;

N (3 dimethylaminopropyl) 2 aza-8,8 diethyl 8-germanspiro [4:5]decane;

N-(3-dimethylaminopropyl) 2 aza 8,8 dipropyl 8-germanspiro [4:5]decane; and

N (3 dimethylaminopropyl) 2 aza 8,8 dibutyl 8-germanspiro [4:5]decane.

Rice et al., J. Heterocycl. Chem., 10(5), 731–735 (1973), (Rice I), disclose the synthesis of N (2-dimethyl aminopropyl) 8,8 dimethyl-2-azaspiro [4,5]decane; N-(2-dimethylaminopropyl)-8,8 diethyl 2 azaspiro [4,5]decane, N-(3 dimethylaminopropyl) 9,9 dimethyl-3 azaspiro [5,5]undecane, and N(3-dimethylaminopropyl) 9,9 diethyl 3-azaspiro [5,5]undecane. Rice I states that biological evaluation of these amines showed significant inhibition of cancer cell growth in human cancer cells grown in tissue culture. There is no disclosure or suggestion in Rice I that such amines have antiarthritic activity.

Rice et al., J. Heterocycl. Chem., 10(5), 737–741 (1973), (Rice II), disclose the synthesis of N-(2-dimethylaminopropyl)-8,8 dimethyl-8-sila-2 azaspiro [4,5]decane and N (3-dimethylaminopropyl) 9,9 dimethyl 9-sila-3-azaspiro [5,5]undecane, and further state that biological evaluation of such compounds indicated cytotoxic action against human cancer cells grown in tissue culture. There is no disclosure or suggestion in Rice II that such compounds have antiarthritic activity.

Rice et al., U.S. Pat. No. 3,256,277, issued June 14, 1966, (Rice III), claim a compound selected from the group consisting of (I) a compound of the formula

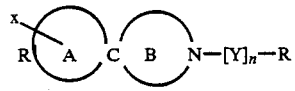

wherein A is a ring of at least 5 ring atoms, all of the ring atoms being carbon atoms except for $R^1$; $R^1$ is selected from the group consisting of oxygen and sulfur; X is selected from the group consisting of at least one of hydrogen, lower alkoxy, lower alkyl, lower alkenyl, cyclo lower alkyl and monocarbocyclic aryl; B is a saturated ring of 5–6 ring atoms, the ring atoms in ring B other than the nitrogen atom being carbon atoms; Y is selected from the group consisting of alkylene and alkenylene of up to 6 carbon atoms; n is 0–1; and R is selected from the group consisting of lower alkyl, lower alkenyl, cyclo lower alkyl, cyclo lower alkenyl, lower and di-lower alkyl and alkenyl amino, saturated heterocyclic selected from the group consisting of morpholino, piperidino, pyrrolidino, piperazino, tetrahydrofuryl and their lower alkyl and alkenyl substituted derivatives, monocarbocyclic aryl, naphthyl, pyridyl, quinolyl, furyl and lower alkoxy; (2) the non-toxic acid addition salts (1); and (3) the non toxic quaternary salts of (1).

Rice III states that such compounds are characterized by their pharmacoloqical activity on the nervous and cardiovascular systems. There is no disclosure or suggestion in Rice III that such compounds have antiarthritic activity.

Rice et al., U.S. Pat. No. 3,282,947, issued November 1, 1966, (Rice IV), claim a compound of the formula

wherein R and $R^1$ are each selected from a different one of the group consisting of:

(a) hydrogen (b) lower alkyl (c) aralkyl selected from the group consisting of pyridyl, lower alkyl and phenyl lower alkyl, (d) di-lower alkylamino lower alkylene, or (e) hydroxy lower alkylene.

Rice IV states that such compounds are valuable as intermediates and that they also have undefined pharmacoloqical activity. There is no disclosure or suggestion in Rice IV that such amines have antiarthritic activity.

Rice et al., J. Med. Chem., 6. 388–402 (1963), (Rice V), disclose preparation of a large group of N-dialkyl amino alkyl azaspiroalkanes, and state that potent (but undefined) pharmacological activity has been observed throughout the group, and that of particular note are the marked growth inhibitory effects of certain members (e.g., 3 (3 dimethylamino propyl 9 t butyl 3 azaspiro [5,5]undecane) on cancer cells in tissue culture and objective clinical effects in human cancer cells. There is no disclosure or suggestion in Rice V that such compounds have antiarthritic activity.

Rice et al., J. Heterocycl. Chem., 1(3), 125–127 (1964), (Rice VI), disclose synthetic routes to various symmetrical and unsymmetrical 3,9 diazaspiro [5,5]undecanes. There is no disclosure or suggestion in Rice VI that such compounds have any bioloqical activity.

Rice et al., U.S. Pat. No. 3,825,546, issued July 23, 1974, (Rice VII), claim a compound having the structural formula:

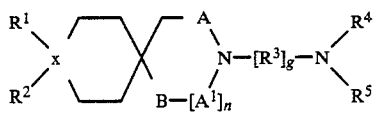

wherein
$R^1$ and $R^2$ are the same or different alkyl groups of 1-4 carbon atoms
X=silicon or germanium
A and $A^1$ are the same and either

n=0 or 1
B=$CH_3$ when n is one and B is the same as A when n is zero
$R^3$ =alkylene or alkenylene
y=2-6 when $R^3$ is alkylene and 3-4 when $R^3$ is alkenylene
$R^4$ and $R^5$ are the same or different lower alkyls having 1-4 carbon atoms, lower alkenyls having 3-4 carbon atoms, or cyclicized together form a heterocyclic group selected from morpholino, pyrrolidino, piperidino and lower alkyl (1-4 carbon atoms) piperazino in which said lower alkyl is attached to a terminal nitrogen atom. Rice VII state that the bisquaternary salts of such compounds exhibit antihypertensive activity and are particularly useful in blocking ganglionic activity in dogs and other animals. There is no disclosure or suggestion in Rice VII that such compounds have antiarthritic activity.

Sanwa KK, European Patent Application Publication Number E0,186,505 A2, published July 2, 1986, claim a composition comprising an organogermanium compound represented by the formula

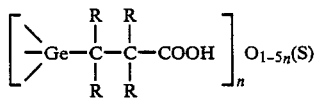

wherein n is an integer of 1 or more, R is hydrogen, alkyl, —COOH, —COOR′, phenyl,

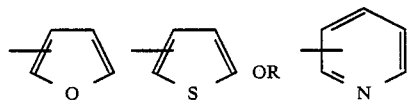

and R′ is a lower alkyl group, and a high molecular carrier for pharmaceutical agents. Sanwa KK disclose that such compounds do not have immunity accelerating action but instead have immunity adjusting or regulating action.

DiMartino et al., *J. Pharmacol. Exp. Therapeut.*, 236, 103-110 (1986) report on the ability of spirogermanium to induce suppressor cells.

Badger et al., *Immunopharmacol.*, 10, 201-207 (1985) report on the generation of suppressor cells in normal rats treated with spirogermanium.

The Australian National University, PCT Patent Application Publication Number WO 85/05031, published Nov. 21, 1985, claim a method of modulating or suppressing the immune response of an animal which comprises the administration of an effective amount of at least one amphiphile which is capable of interacting at the surface of a cell to modify the surface properties thereof so as to inhibit or modify recognition of an antigen by the altered cell. Preferably, the amphiphile is a cationic surfactant, such as a double chained quarternary ammonium surfactant.

Gerschickter Fund, British Patent Application Number 929,739, published June 26, 196, disclose azaspirane compounds of the structure

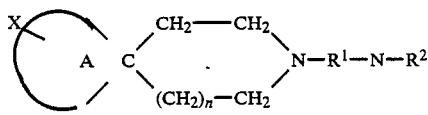

wherein A is a mono or bicyclic carbon ring of at least 5 carbon atoms, X is selected from one or more of hydrogen, alkyl and alkoxy, n is 0 or 1, $R^1$ is an alkylene chain of 2 to 6 carbon atoms, or an alkylene chain if 2 to 6 carbon atoms substituted by a hydroxyl group on a carbon stom at least beta to either nitrogen, and $R^2$ is dialkyl, each alkyl group of which has 1 to 6 carbon atoms, or an alkylene chain forming, together with the nitrogen atom to which it is attached, a morpholine, piperidine, pyrrolidine, or piperazine ring, or an alkyl-substituted derivative of any of these containing from 1 to 6 carbon atoms in the substituent group, and the non-toxic acid addition salts thereof. The Gerschickter patent also specifically discloses
N-(3 dimethylaminopropyl) 9 t butyl 3-azaspiro(5:5)undecane.

The Gerschickter patent also discloses that such compounds are useful for their pharmacoloqical activity on the nervous and cardiovascular system.

SUMMARY OF THE INVENTION

This invention relates to a compound of the formula:

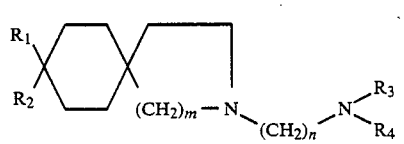

Formula (IA)

wherein:
n is 3-7;
m is 1 or 2;
$R_1$ and $R_2$ are the same or different and are selected from hydrogen or straight chain, branched chain or cyclic alkyl, provided that the total number of carbon atoms contained by $R_1$ and $R_2$ when taken together is 4-10; or $R_1$ and $R_2$ are joined together to form a cyclic alkyl group containing 3-7 carbon atoms;
$R_3$ and $R_4$ are the same or different and are selected from hydrogen or straight chain alkyl containing 1-3 carbon atoms; or $R_3$ and $R_4$ are joined together to form a cyclic alkyl group containing 4–7 carbon atoms;

provided that when $R_1$ and $R_2$ are $CH_3CH_2$, $R_3$ and $R_4$ are $CH_3$ and m is 1 or 2, n is other than 3; and further provided that when $R_1$ is H; $R_2$ is $(CH_3)_3C$; $R_3$ and $R_4$ are $CH_3$ and m is 1 or 2, n is other than 3; and further provided that when $R_2$ is H; $R_1$ is $(CH_3)_3C$; $R_3$ and $R_4$ are $CH_3$ and m is 2, n is other than 3;

or a pharmaceutically acceptable salt, hydrate or solvate thereof.

This invention also relates to a compound of the formula:

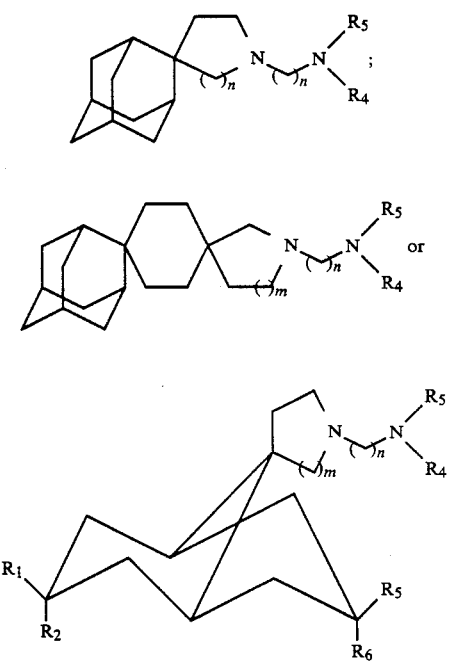

Formula (II)

wherein:

n is 3–7;

m is 1 or 2;

$R_1$, $R_2$, $R_5$, and $R_6$ are the same or different and are selected from hydrogen or methyl;

$R_3$ and $R_4$ are the same or different and are selected from hydrogen or straight chain alkyl containing 1–3 carbon atoms; or $R_3$ and $R_4$ are joined together to form a cyclic alkyl group containing 4–7 carbon atoms, or a pharmaceutically acceptable salt, hydrate or solvate thereof.

This invention relates to a pharmaceutical composition comprising a pharmaceutically acceptable carrier or diluent and an effective amount of a compound of the formula:

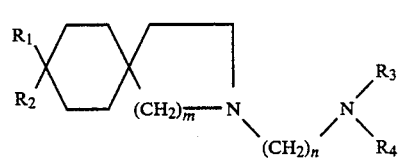

Formula (I)

wherein:

n is 3–7;

m is 1 or 2;

$R_1$ and $R_2$ are the same or different and are selected from hydrogen or straight chain, branched chain or cyclic alkyl, provided that the total number of carbon atoms contained by $R_1$ and $R_2$ when taken together is 4–10; or $R_1$ and $R_2$ are joined together to form a cyclic alkyl group containing 3–7 carbon atoms;

$R_3$ and $R_4$ are the same or different and are selected from hydrogen or straight chain alkyl containing 1–3 carbon atoms; or $R_3$ and $R_4$ are joined together to form a cyclic alkyl group containing 4–7 carbon atoms, or a pharmaceutically acceptable salt, hydrate or solvate thereof.

This invention also relates to a pharmaceutical composition comprising a pharmaceutically acceptable carrier or diluent and an effective amount of a compound of Formula (II).

This invention also relates to a method of treating an animal in need of immunomodulation which comprises administering an effective amount of a compound of Formula (I) or Formula (II) or a pharmaceutically acceptable salt, hydrate or solvate to such animal.

It will be recoqnized by one of skill in the art that all the compounds of Formula (IA) are embraced by the scope of Formula (I).

Preferred compounds of Formula (I) and Formula (II) are listed in Table 1, infra. Especially preferred is Compound #02 of Table 1.

Pharmaceutically acceptable salts and their preparation are well known to those of skill in the art. Preferred pharmaceutically acceptable salts for compounds of Formula (I) and Formula (II) include, but are not limited to, hydrochloride, dihydrochloride, citrate, maleate, lactate, hydrobromide, and sulfate. The dihydrochloride salt is especially preferred.

The compounds of Formula (I) and (II) may form hydrates or solvates. It is known to those of skill in the art that charged compounds form hydrated species when lyophilized with water, or form solvated species when concentrated in a solution with an appropriate organic solvent.

Compounds of Formula (I) and Formula (II) may be prepared by the methods described in the Examples, infra.

All compounds of Formula (I) and Formula (II) are useful for treating an animal, including humans, in need of immunomodulation. Such immunomodulation activity was ascertained utilizing the adjuvant induced arthritis assay in rats which is summarized in Table I, and/or a suppressor cell activity assay which is summarized in Table II.

TABLE 1

Activity of Compounds of Formula (I) and Formula (II) in the Adjuvant Induced Arthritis Assay

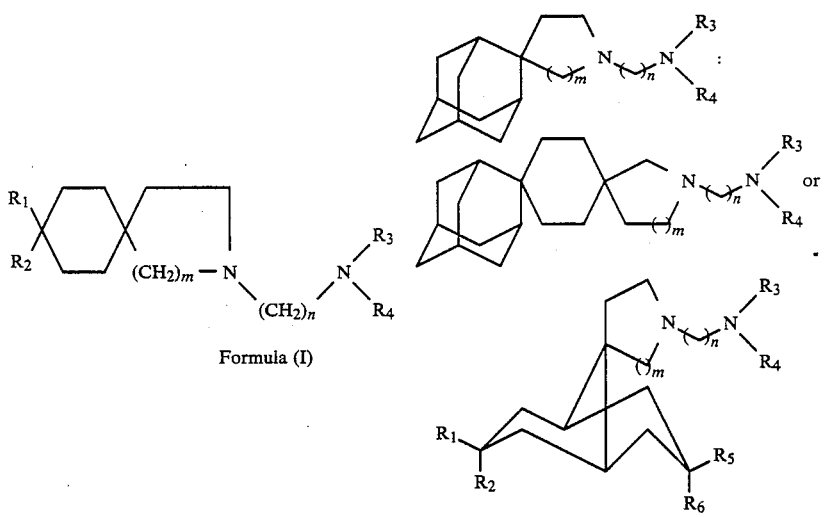

Formula (I)

| # (a) | m | n | $R_1$ | $R_2$ | $R_3$ | $R_4$ | (b) | (c) |
|---|---|---|---|---|---|---|---|---|
| 01 | 1 | 3 | $CH_3CH_2$ | $CH_3CH_2$ | $CH_3$ | $CH_3$ | 0.57 | 30 |
| 02 | 1 | 3 | $CH_3CH_2CH_2$ | $CH_3CH_2CH_2$ | $CH_3$ | $CH_3$ | 1.35 | 30 |
| 03 | 1 | 3 | $CH_3(CH_2)_2CH_2$ | $CH_3(CH_2)_2CH_2$ | $CH_3$ | $CH_3$ | 0.88 | 30 |
| 04 | 1 | 3 | $CH_3(CH_2)_3CH_2$ | $CH_3(CH_2)_3CH_2$ | $CH_3$ | $CH_3$ | 0.41 | 30 |
| 05 | 1 | 3 | $(CH_3)_2CHCH_2$ | $(CH_3)_2CHCH_2$ | $CH_3$ | $CH_3$ | 0.97 | 30 |
| 06 | 2 | 3 | $CH_3CH_2CH_2$ | $CH_3CH_2CH_2$ | $CH_3$ | $CH_3$ | 0.90 | 30 |
| 07 | 1 | 3 | $CH_3CH_2CH_2$ | $CH_3CH_2CH_2$ | H | H | 1.52 | 30 |
| 08 | 1 | 3 | $CH_3CH_2CH_2$ | $CH_3CH_2CH_2$ | $CH_3$ | H | 1.02 | 30 |
| 09 | 1 | 3 | $CH_3CH_2(CH_3)CH$ | $CH_3$ | $CH_3$ | $CH_3$ | 1.27 | 30 |
| 10 | 1 | 3 | $CH_3$ | $CH_3CH_2(CH_3)CH$ | $CH_3$ | $CH_3$ | 2.84 | 60 |
| 11 | 1 | 3 | $CH_3CH_2$ | $CH_3(CH_2)_2CH_2$ | $CH_3$ | $CH_3$ | 1.15 | 15 |
| 12 | 1 | 3 | $CH_3(CH_2)_2CH_2$ | $CH_3CH_2$ | $CH_3$ | $CH_3$ | 4.00 | 30 |
| 13 | 1 | 3 | H | $CH_3(CH_2)_3CH_2$ | $CH_3$ | $CH_3$ | 0.78 | 30 |
| 14 | 1 | 3 | H | cyclohexyl | $CH_3$ | $CH_3$ | 0.98 | 30 |
| 15 | 1 | 3 | H | $(CH_3)_3C$ | $CH_3$ | $CH_3$ | 0.31 | 30 |
| 16 | 1 | 3 | $(CH_3)_3C$ | H | $CH_3$ | $CH_3$ | 0.90 | 30 |
| 17 | 1 | 3 | —$CH_2CH_2CH_2CH_2CH_2CH_2$— | | $CH_3$ | $CH_3$ | 1.70 | 60 |
| 18 | 1 | 3 | $CH_3CH_2CH_2$ | $CH_3CH_2CH_2$ | $CH_3CH_2$ | $CH_3CH_2$ | 1.42 | 30 |
| 19 | 1 | 3 | $CH_3CH_2CH_2$ | $CH_3CH_2CH_2$ | —$CH_2(CH_2)_3CH_2$— | | 1.89 | 30 |
| 20 | 1 | 4 | $CH_3CH_2CH_2$ | $CH_3CH_2CH_2$ | $CH_3$ | $CH_3$ | 0.45 | 30 |
| 21 | 1 | 5 | $CH_3CH_2CH_2$ | $CH_3CH_2CH_2$ | $CH_3$ | $CH_3$ | 0.82 | 30 |
| 22 | 1 | 6 | $CH_3CH_2CH_2$ | $CH_3CH_2CH_2$ | $CH_3$ | $CH_3$ | 1.28 | 30 |
| 23 | 1 | 7 | $CH_3CH_2CH_2$ | $CH_3CH_2CH_2$ | $CH_3$ | $CH_3$ | 1.57 | 30 |
| 24 | 1 | 3 | Spiroadamantane | | $CH_3$ | $CH_3$ | 0.76 | 30 |
| 25 | 1 | 3 | Adamantane | | $CH_3$ | $CH_3$ | 0.33 | 30 |
| 26 | 1 | 3 | Bicyclo(3.3.1)nonan-9-one | | $CH_3$ | $CH_3$ | 0.92 | 30 |
| 27 | 1 | 3 | $CH_3CH_2CH_2$ | $CH_3CH_2CH_2$ | —$CH_2(CH_2)_2CH_2$— | | 1.03 | 30 |
| 28 | 1 | 6 | $CH_3CH_2CH_2$ | $CH_3CH_2CH_2$ | —$CH_2CH_2)_2CH_2$— | | .63 | 30 |
| 29 | 1 | 6 | $CH_3CH_2CH_2$ | $CH_3CH_2CH_2$ | —$CH_2(CH_2)_3CH_2$— | | n.t. | |
| 30 | 1 | 3 | $CH_3CH_2$ | $CH_3CH_2$ | —$CH_2(CH_2)_2CH_2$— | | n.t. | |
| 31 | 1 | 3 | $CH_3CH_2$ | $CH_3CH_2$ | —$CH_2(CH_2)_3CH_2$— | | n.t. | |
| 32 | 1 | 3 | $CH_3CH_2$ | $CH_3CH_2$ | $CH_3CH_2$ | $CH_3CH_2$ | n.t. | | n.t. = not tested
(a) # = compound number. Compound numbers 01 to 23 and 27 to 32 belong to
Formula (I) compound numbers
(b) AA Rat % Right paw inhibition (Day 16) Relative to Spirogermanium (d,e)
(c) Dose (mglkg)
(d) Test Elaboration/Modification
Adjuvant arthritis is produced by a single intradermal injection of 0.75 mgs. of *M. butyricum* suspended in white paraffin oil (light N.F.) into a hindpaw (left) footpad. The injected paw becomes inflamed (increased volume) and reaches maximal size within 3–5 days (primary lesion). The animals exhibit a decrease in body weight gain during this initial period. The adjuvant arthritis (secondary lesion) occurs after a delay of approximately 10 days and is characterized by inflammation of the non-injected sites (right hind paw), decrease in body weight, and further increases in the volume of the injected hind paw. Test compounds are administered daily, beginning on the day of the adjuvant injection, for either 17 days, exclusive of days 4, 5, 11 and 12, for 11 consecutive days or for 17 consecutive days. Drug activity on the primary (left paw-day 3) and secondary (right hind paw-day 16) lesion is determined by comparing paw volumes of the treated group with a control arthritic (vehicle) group. Hind paw volumes are measured by immersing the paw into a mercury of water reservoir and recording the subsequent displacement.
(e) Definition of Significant Activity(*)
A compound is considered to have anti-athritic activity if it produces a statistically significant ($p < 0.05$) decrease of thirty percent (30%) or more in the inflamed hind paw volumes and/or

TABLE 1-continued
Activity of Compounds of Formula (I) and Formula (II) in the Adjuvant Induced Arthritis Assay

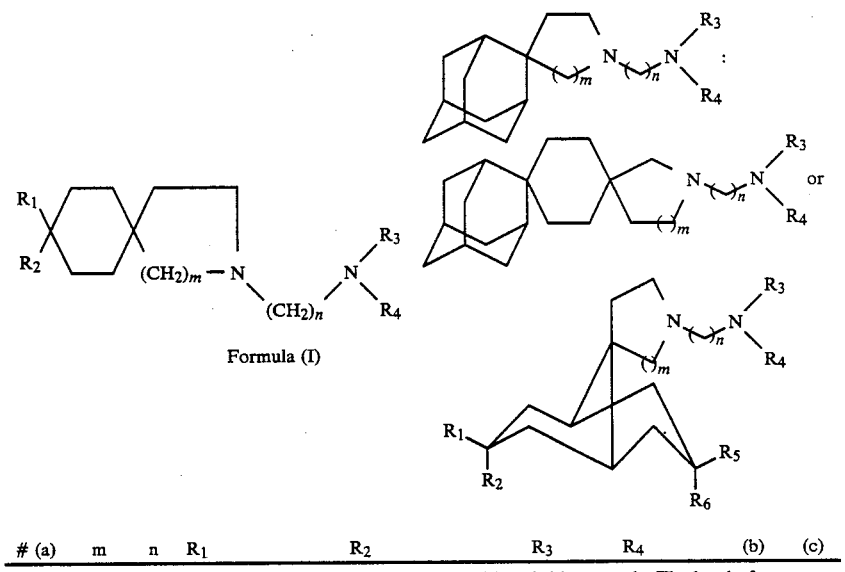

Formula (I)

| # (a) | m | n | $R_1$ | $R_2$ | $R_3$ | $R_4$ | (b) | (c) |
|---|---|---|---|---|---|---|---|---| the arthritic scores of the treated groups when compared with arthritic controls. The level of significant difference between treated groups and control groups is determined by the student "t" test. Body weight changes from day 0 are also statistically compared to the arthritic control group. % inhibition of a compound of Formula (I) and Formula (II) on Day 16 (right paw) is divided by spirogermanium activity on Day 16 to yield a relative activity profile. Note: In some of the experiments, Compound #2 of Table 1 was used as the standard instead of spirogermanium (SG). Compound #2 is 1.35 times better than SG in the AA rat model. Therefore, all compound activities were normalized to SG by multiplying by this factor.

TABLE 2
SUPPRESSOR CELL ACTIVITY BY COMPOUNDS OF FORMULA (I) AND FORMULA (II)[c]

| Compound[a] Number | Dose | Suppressor Cell Activity[b] |
|---|---|---|
| 1 | 30 mg/kg | 88 |
| 2 | 30 mg/kg | 172 |
| 3 | 30 mg/kg | 176 |
| 4 | 7.5 mg/kg | 118 |
| 5 | 30 mg/kg | 162 |
| 6 | 30 mg/kg | 158 |
| 7 | 30 mg/kg | 217 |
| 8 | 15 mg/kg | 67 |
| 9 | 30 mg/kg | 132 |
| 10 | 30 mg/kg | 112 |
| 11 | 15 mg/kg | 139 |
| 12 | 15 mg/kg | 172 |
| 13 | 15 mg/kg | 96 |
| 14 | | n.t. |
| 15 | | n.t. |
| 16 | | n.t. |
| 17 | | n.t. |
| 18 | 30 mg/kg | 201 |
| 19 | 30 mg/kg | 241 |
| 20 | 30 mg/kg | 178 |
| 21 | 30 mg/kg | 177 |
| 22 | 15 mg/kg | 141 |
| 23 | 30 mg/kg | 146 |
| 24 | 30 mg/kg | 84 |
| 25 | | n.t. |
| 26 | 30 mg/kg | 7 |
| 27 | | n.t. |
| 28 | | n.t. |
| 29 | | n.t. |
| 30 | | n.t. |
| 31 | | n.t. |
| 32 | | n.t. | n.t. = not tested
[a]See Table 1 for compound structure
[b]Suppressor cell activity is calculated in the following manner. A plot of percent suppression (dependent variable) versus the logarithm (base e) of the number of suppressor cells (independent variable) was generated and the area under the curve (AUC) represented by the data points of this plot was determined via the trapezoidal rule. The trapezoidal rule provides AUC by means of the summation of the areas of the trapezoids whose vertices are located at adjacent values of the independent variable. All data was normalizd to spirogermanium (SG). In some experiments, Compound #2 of Table 1 was used as the standard instead of spirogermanium. Compound #2 is 1.72 times better than SG in the suppressor cell assay. Therefore, all compound activities were normalized to SG by multiplying by this factor (i.e., SG = 100; compound #2 = 172).
[c]The assay employed to test compounds of Formula (I) and Formula (II) for suppressor cell generation ability is the one described by Badger et al., Immunopharmacology, 10, 201–207 (1985). Briefly: Male inbred Lewis rats were obtained from Charles River Breeding Laboratories (Wilmington, MA, U.S.A.). Rats were maintained on water and routine rat chow and were used at 6 to 8 weeks of age (160–180 g). Within any given experiment only rats of the same age, strain and sex wereused. Concanavalin A (Con A) was obtained from Pharmacia Fine Chemicals (Piscataway, NJ) and dissolved in RPMI-1640 (Flow Laboratories, Rockville, MD) that was supplemented with penicillin, streptomycin and L-glutamine (Grand Island Biological Co., Grand Island, NY) and with 10% heat-inactivated (56° C., 30 min) fetal calf serum. This medium will hereafter be referred to as RPMI 10. For in vivo treatment compounds were dissolved in 0.5% tragacanth and administered orally once a day.Spleen cells from animals treated with compounds of Formula (I) and Formula (II) were established in RPMI-10 at $5 \times 10^6$/ml. Co-culture experiments for the determination of suppressor cells were carried out by first adding varying numbers of the putative suppressor cells (0.15 to $5 \times 10^5$) to 96-well round bottomed microtiter plates (Linbro, Flow Labs) in 100 µl of RPMI-10. These cells were then irradiated (2000Rad) in a Gamma cell 40 with a 137Cs source. To these cultures were added $5 \times 10^5$ normal cells and an optimal concentration of Con A (5 µg/ml) and the final volume was adjusted to 200 µl. Cell cultures were incubated for 72 hours at 37° C. in a 5% $CO_2$ atmosphere and pulsed with 0.5 µCi [$^3$H]thymidine (specific activity 1.9 Ci/mmol; Schwarz/Mann, Orangeburg, NY) for the last 16 hours of culture. The cells wereharvested on an automated multiple sample harvester and cell-associated radioactivity counted in a Beckman liquid scintillation counter. Suppressive activity is determined by comparing cpm of co-cultures containing untreated cells with those containing treated cells by Student's t test.

Table 2, above, shows the act compounds of Formula (I) and Formula (II) in generating suppressor cells in vivo. By "generating suppressor cells" is meant that the compound induces a suppressor cell like activity, e.q., a cell that is capable of suppressing the immune function of a normal cell in an in vitro co culture assay such as that of Rich and Pierce, *J Exp. Med.*, 137, 649 (1973). The spleen cells from treated animals were established at varying concentrations with normal cells. These suppressor cells are also capable of inhibiting mixed lymphocyte reactions, antibody synthesis and delayed type hypersensitivity responses.

This invention also relates to a pharmaceutical composition comprising a pharmaceutically acceptable carrier or diluent and an effective amount of a compound of Formula (I) or Formula (II).

A compound of Formula (I) or Formula (II) is administered in conventional dosage form prepared by combining a therapeutically effective amount (i.e., an effective immunomodulatory amount) of a compound of Formula (I) or Formula (II) ("active ingredient") with standard pharmaceutical carriers or diluents according to conventional procedures. These procedures may involve mixing, granulating and compressing or dissolving the ingredients as appropriate to the desired preparation.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time delay material well known to the art, such as gleyceryl monostearate or glyceryl distearate alone or with a wax, ethylcellulose, hydroxypropylmethylcellulose, methylmethacrylate and the like.

A wide variety of pharmaceutical forms can be employed. Thus, if a solid carrier is used, the preparation can be tableted, placed in a hard gelatin capsule in powder or pellet form or in the form of a troche or lozenqe. The amount of solid carrier will vary widely but preferably will be from about 25 mg to about 1 q. If a liquid carrier is used, the preparation will be in the form of a syrup, emulsion, soft gelatin capsule, sterile injectable solution or suspension in an ampule or vial or nonaqueous liquid suspension.

To obtain a stable water soluble dose form, a pharmaceutically acceptable salt of a compound of Formula (I) or Formula (II) is dissolved in an aqueous solution of an organic or inorqanic acid, such as a 0.3M solution of succinic acid, or, preferably, citric acid. If a soluble salt form is not available, the compound of Formula (I) or Formula (II) is dissolved in a suitable cosolvent or combinations thereof. Examples of such suitable cosolvents include, but are not limited to, alcohol, propylene glycol, polyethylene glycol 300, polysorbate 80, glycerin and the like in concentrations ranging from 0-60% of the total volume.

Preferably, each parenteral dosage unit will contain the active inqredient in an amount of from about 0.1 mg to about 500 mg. Preferably each oral dosage unit will contain the active inqredient in an amount of from about 1 mg to about 1000 mg.

The compounds of Formula (I) and Formula (II) are all active as immunomodulatory agents in animals, including humans, in need of such immunomodulation when such compounds are administered to such animals according to the method of this invention. By the term "immunomodulatory agent" is meant that each of the compounds of Formula (I) or Formula (II) is capable of inducing immune suppression via induction of suppressor cell like activity (as evidenced by their activity in the suppressor cell assay described in Table 2) and/or via production of a statistically significant decrease in the inflammation of the immune system response mediated secondary lesion in the adjuvant induced arthritis assay (See, Table 1). Indications for therapy using an immunomodulatory agent include, but are not limited to, the treatment of the following disease states:

rheumatoid arthritis
systemic lupus erythematosis
multiple sclerosis
acute transplantation/graft rejection
myasthenia gravis
progressive systemic sclerosis
multiple myeloma
atopic dermatitis
hyperimmunoglobin E
hepatitis B antigen negative chronic active hepatitis
Hashimoto's thyroiditis
Familial Mediterranean fever
Grave's disease
autoimmune hemolytic anemia
primary biliary cirrhosis
inflammatory bowel disease This invention also relates to use of a compound of Formula (I) or Formula (II) in treating an animal in need of immunomodulation, including humans and other mammals, which comprises administering to such animal an effective amount of a Formula (I) or Formula (II) compound or a pharmaceutically acceptable salt, hydrate or solvate. By the term "treating" is meant prophylactic or therapeutic therapy. The Formula (I) or Formula (II) compound is administered to an animal in need of immunomodulatory treatment in an amount sufficient to produce such immunomodulation to a therapeutic or prophylactic degree. Such Formula (I) or Formula (II) compound can be administered to such animal in a conventional dosage form prepared by combining the Formula (I) or Formula (II) compound with a conventional pharmaceutically acceptable carrier or diluent according to known techniques. It will be recoqnized by one of skill in the art that the form and character of the pharmaceutically acceptable carrier or diluent is dictated by the amount of active ingredient with which it is to be combined, the route of administration and other well known variables.

The route of administration of the Formula (I) or Formula (II) compound may be oral, parenteral, by inhalation or topical. The term parenteral as used herein includes intravenous, intramuscular, subcutaneous, rectal, vaginal or intraperitoneal administration. The subcutaneous and intramuscular forms of parenteral administration are generally preferred. The daily parenteral dosage regimen for a compound will preferably be from about 0.1 mg to about 1,000 mg per day. The daily oral dosage regimen will preferably be from about 1 mg to about 2,000 mg.

The compounds for Formula (I) and Formula (II) may also be administered by inhalation. By "inhalation" is meant intranasal and oral inhalation administration. Appropriate dosage forms for such administration, such as an aerosol formulation or a metered dose inhaler, may be prepared by conventional techniques. The preferred daily dosage amount of a compound of Formula (I) or Formula (II) administered by inhalation is from about 10 mg to about 100 mg per day.

The compounds of Formula (I) and Formula (II) may also be administered topically.

The amount of a compound of Formula (I) or Formula (II) (hereinafter referred to as the active ingredient) required for therapeutic effect on topical administration will, of course, vary with the compound chosen, the nature and severity of the inflammatory condition and the animal undergoing treatment, and is ultimately at the discretion of the physician. A suitable immunomodulatory dose of a compound of Formula (I) or Formula (II) is 1.5 µg to 500 mg of base per kilogram bodyweight for topical administration, the most preferred dosage being 1 µg to 50 mg/kg of animal bodyweight, for example 5 µg to 25 mg/kg; administered two or three times daily. For application to the skin, from 1 µg to several mg of active ingredient may be applied per application, preferably from 10 µg to 100 µg per application.

By topical administration is meant non-systemic administration and includes the application of a compound of Formula (I) or Formula (II) externally to the epidermis, to the buccal cavity and instillation of such a compound into the ear, eye and nose, and where the compound does not significantly enter the blood stream. By systemic administration is meant oral, intravenous, intraperitoneal and intramuscular administration.

While it is possible for an active inqredient to be administered alone as the raw chemical, it is preferable to present it as a pharmaceutical formulation. The active ingredient may comprise, for topical administration, from 0.001% to 10% w/w, e.q. from 1% to 2% by weight of the formulation although it may comprise as much as 10% w/w but preferably not in excess of 5% w/w and more preferably from 0.1% to 1% w/w of the formulation.

The topical formulations of the present invention, both for veterinary and for human medical use, comprise an active ingredient together with one or more acceptable carrier(s) therefore and optionally any other therapeutic inqredient(s). The carrier(s) must be 'acceptable' in the sense of being compatible with the other ingredients of the formulation and not deleterious to the recipient thereof.

Formulations suitable for topical administration include liquid or semi liquid preparations suitable for penetration through the skin to the site of where treatment is required such as: liniments, lotions, creams, ointments or pastes, and drops suitable for administration to the eye, ear or nose.

Drops according to the present invention may comprise sterile aqueous or oily solutions or suspensions and may be prepared by dissolving the active inqredient in a suitable aqueous solution of a bactericidal and/or fungicidal agent and/or any other suitable preservative, and preferably including a surface active agent. The resulting solution may then be clarified by filtration, transferred to a suitable container which is then sealed and sterilized by autoclaving or maintaining at 90–100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), bencalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi solid formulations of the active inqredient for external application. They may be made by mixing the active inqredient in finely-divided or powered form, alone or in solution or suspension in an aqueous or non aqueous fluid, with the aid of suitable machinery, with a greasy or non qreasy basis. The basis may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol or macrogols. The formulation may incorporate any suitable surface active agent such as an anionic, cationic or non ionic surfactant such as sorbitan esters or polyoxyethylene derivatives thereof. Suspending agents such as natural gums, cellulose derivatives or inorqanic materials such as silicaceous silicas, and other ingredients such as lanolin, may also be included.

It will be recoqnized by one of skill in the art that the optimal quantity and spacing of individual dosages of the Formula (I) or Formula (II) compound will be determined by the nature and extent of the condition being treated, the form, route and site of administration, and the particular animal being treated, and that such optimums can be determined by conventional techniques. It will also be appreciated by one of skill in the art that the optimal course of treatment, i.e., the number of doses of the Formula (I) or Formula (II) compound given per day for a defined number of days, can be ascertained by those skilled in the art using conventional course of treatment determination tests.

Without further elaboration, it is believed that one skilled in the art can, using the preceding description, utilize the present invention to its fullest extent. The following Examples are, therefore, to be construed as merely illustrative and not a limitation of the scope of the present invention in any way.

EXAMPLES

1. Composition Examples

EXAMPLE A—CAPSULE COMPOSITION

A pharmaceutical composition of this invention in the form of a capsule is prepared by filling a standard two piece hard gelatin capsule with 50 mg of a compound of Formula (I) or Formula (II), in powdered form, 110 mg of lactose, 32 mg of talc and 8 mg of magnesium stearate.

EXAMPLE B—INJECTABLE PARENTERAL COMPOSITION

A pharmaceutical composition of this invention in a form suitable for administration by injection is prepared by stirring 1.5% by weight of a compound of Formula (I) or Formula (II) in 10% by volume propylene glycol and water. The solution is sterilized by filtration.

EXAMPLE C—OINTMENT COMPOSITION

Compound of Formula (I) or Formula (II) 1.0 g
White soft paraffin to 100.0 g

The compound of Formula (I) or Formula (II) is dispersed in a small volume of the vehicle and gradually incorporated into the bulk of the vehicle to produce a smooth, homogeneous product. Collapsible metal tubes are then filled with the dispersion.

EXAMPLE D—TOPICAL CREAM COMPOSITION

Compound of Formula (I) or Formula (II) 1.0 g
Polawax GP 200 20.0 g
Lanolin Anhydrous 2.0 g
White Beeswax 2.5 g
Methyl hydroxybenzoate 0.1 g
Distilled Water to 100.0 g The polawax, beeswax and lanolin are heated together at 60° C. A solution of methyl hydroxybenzoate is added and homogenization is achieved using high speed stirring. The temperature is then allowed to fall to 50° C. The compound of Formula (1) or Formula (II) is then added and dispersed throughout, and the composition is allowed to cool with slow speed stirring.

EXAMPLE E—TOPICAL LOTION COMPOSITION

Compound of Formula (1) or Formula (II) 1.0 g
Sorbitan Monolaurate 0.6 g
Polysorbate 20 0.6 g
Cetostearyl Alcohol 1.2 g
Glycerin 6.0 g
Methyl Hydroxybenzoate 0.2 g
Purified Water B.P. to 100.00 ml The methyl hydroxybenzoate and glycerin are dissolved in 70 ml of the water at 75°. The sorbitan monolaurate, polysorbate 20 and cetostearyl alcohol are melted together at 75° C and added to the aqueous solution. The resulting emulsion is homoqenized, allowed to cool with continuous stirring and the compound of Formula (I) or Formula (II) is added as a suspension in the remaining water. The whole suspension is stirred until homogenized.

EXAMPLE F—EYE DROP COMPOSITION

Compound of Formula (I) or Formula (II) 0.5 g
Methyl Hydroxybenzoate 0.01 g
Propyl Hydroxybenzoate 0.04 g
Purified Water B.P. to 100.00 ml (B.P. = British Pharmacopia)

The methyl and propyl hydroxybenzoates are dissolved in 70 ml purified water at 75° C. and the resulting solution is allowed to cool. The compound of Formula (I) or Formula (II) is then added, and the solution is sterilized by filtration through a membrane filter (0.22 mu m pore size) and packed aseptically into suitable sterile containers.

EXAMPLE G—COMPOSITION FOR ADMINISTRATION BY INHALATION

For an aerosol container with a capacity of 15–20 ml: Mix 10 mg of a compound of Formula (I) or Formula (II) with 0.2–0.2% of a lubricatinq agent, such as polysorbate 85 or oleic acid, and disperse such mixture in a propellant, such as freon, preferably in a combination of (1,2 dichlorotetrafluoroethane) and difluorochloromethane and put into an appropriate aerosol container adapted for either intranasal or oral inhalation administration.

EXAMPLE H—COMPOSITION FOR ADMINISTRATION BY INHALATION

For an aerosol container with a capacity of 15–20 ml: Dissolve 10 mg of a compound of Formula (I) or Formula (II) in ethanol (6–8 ml), add 0.1–0.2% of a lubricating agent, such as polysorbate 85 or oleic acid; and disperse such in a propellant, such as freon, preferably a combination of (1,2 dichlorotetrafluoroethane) and difluorochloromethane, and put into an appropriate aerosol container adapted for either intranasal or oral inhalation administration.

II. Synthetic Examples

In the following Examples, temperature is in degrees Centigrade (° C). Elemental analyses and melting points of the compounds of Formula (I) and Formula (II) prepared according to the method of the following synthetic examples are listed in Tables 3 and 4.

Sodium hydride, trimethyl sulfoxonium iodide, methyl vinyl ketone, ethyl cyanoacetate, morpholine, lithium aluminum hydride, boron trifluoride etherate, heptan 4 one, nonan 5 one, undecan 6 one, 4 (1,1 dimethylethyl)cyclohexanone, 4 cyclohexylcyclohexanone. valeraldehyde, allyl bromide, dodecanal, 2.3 dimethylvaleraldehyde, 2-ethylbutyraldehyde, 2 ethylhexanal, adamantanone, bicyclo(3.3.1)nonan 9-one, 3-dimethylaminopropylamine, 3 diethylaminopropylamine, diisobutylamine, 2, 6 dimethylheptan 4 one, cycloheptanone, acidic anhydride, Triton B and 3-methylaminopropylamine were purchased from Aldrich Chemicals (Milwaukee, Wis., U.S.A.). 3-(1 piperidine)propylamine was synthesized by the lithium aluminum hydride reduction of 1 piperidinepropionitrile (Aldrich Chemicals; Milwaukee Wis., U.S.A.).

4-Dimethylaminobutylamine and 6-dimethylaminohexylamine were purchased from Pfaltz and Bauer (Waterbury, Conn., U.S.A.). 5 Dimethylaminopentylamine and 7 dimethylaminoheptylamine were purchased from Karl Industries (Aurora, Ohio, U.S.A.).

3 aminopropanitrile and 3-(1 pyrrolidine)propylamine were purchased from Alfa Chemicals (Danvers, Mass., U.S.A.). 6 (1 Piperidine)hexylamine was prepared in two steps by the alkylation of 6 bromohexylamine (Aldrich Chemicals) with piperidine and subsequent lithium aluminium hydride reduction. 6-(1 Pyrolidine)hexylamine were similarly prepared from the requisite bromonitriles and pyrrolidine.

Section 1: Synthesis of 4,4-Disubstituted Cyclohexanone

Scheme 1 outlines the generic synthesis of 4,4-disubstituted cyclohexanones starting from either a commercially available ketone or α,α-disubstituted aldehyde.

Scheme 1

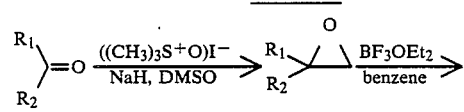

-continued
Scheme 1

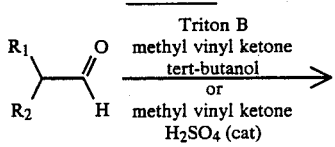

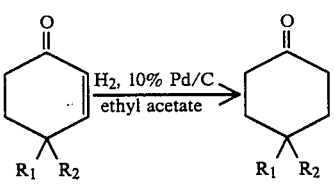

Examples 1-5, below, describe specifically the synthesis of 4,4-dipropylcyclohexanone from heptan 4 one however this methodology has been used to prepare the following cyclohexanones startinq from the listed commercially available ketones:

| ketone | cyclohexanone |
|---|---|
| 2,6-dimethylheptan-4 one | 4,4 bis(2-methylpropyl)- |
| nonan-5-one | 4,4-dibutyl- |
| undecan-6-one | 4,4-dipentyl- |
| cycloheptanone | spiro[5.6]dodecan-3-one |
| 2-adamantanone | spiro-(cyclohexane-1,2'-tricyclo-[3.3.1.1$^{3,7}$]decane-4-one |

In the following cases the α,α-disubstituted aldehydes were available and the 4,4 disubstituted cyclohexanones were synthesized:

| aldehyde | cyclohexanone |
|---|---|
| 2-ethylbutyraldehyde | 4,4-diethyl- |
| 2-ethylhexanal | 4-butyl-4-ethyl- |
| 2,3-dimethylvaleraldehyde | 4-methyl-4-(1 methylpropyl)- |

A second better yielding route specifically for the synthesis of 2 propylpentanal is described in Scheme 2. The procedures are outlined in Examples 5 and 6.

Scheme 2

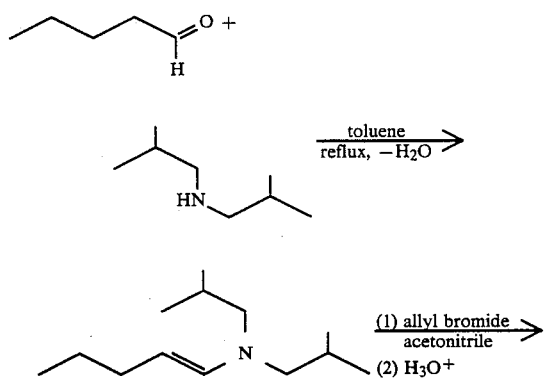

-continued
Scheme 2

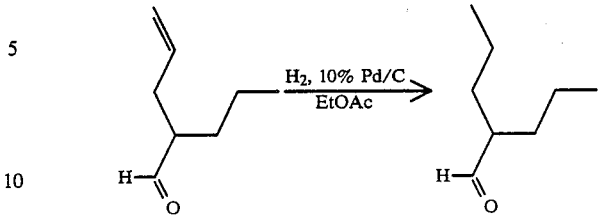

Example 1: 2 Propyl 1,2 epoxypentane Dimethyl sulfoxide (1 1/mole) was slowly added to a mechanically stirred mixture of sodium hydride (1.1 equivalents) and trimethylsulfoxonium iodide (1 equivalent) under an inert atmosphere. Vigorous hydrogen evolution ensued and on completion of gas evolution heptan 4 one(0.4 equivalents) was added and the reaction mixture was heated at 75° for 3-24 hours.

The reaction mixture was poured into water (3-5 volumes) and extracted with ethyl acetate. The organic extract was dried with magnesium sulfate, filtered and concentrated to give the desired product (85% yield) which was used without further purification.

Example 2: 2 PROPYLPENTANAL

To a vigorously stirred solution of 2 propyl 1,2 epoxypentane (1 equivalent), prepared as described in Example 1, in benzene cooled to 0° was added a solution of boron trifluoride etherate (0.5 equivalents) in benzene. The reaction mixture was stirred for 1 min and was quenched by the addition of water. Following separation of the phases, the organic phase was washed with saturated aqueous sodium bicarbonate and water, dried with magnesium sulfate, filtered and concentrated to give a colorless oil. The oil was distilled to give the desired product as a colorless oil; 75% yield; boiling point (b.p) 60-63° /0.1 mm.

EXAMPLE 3: 4,4 DIPROPYLCYCLOHEX-2 ENONE

Method 1: To a solution of a base (Triton B, 0.05 equivalents) in tert-butanol was added concurrently from separate addition funnels 2 propylpentanal (1 equivalent), prepared as described in Example 2, and methylvinylketone (1.2 equivalents) over 1 hour so that the temperature is maintained below 15° . To the reaction mixture is subsequently added concentrated hydrochloric acid (0.02-0.2 equivalents) and the solution was concentrated to a viscous oil. The oil was dissolved in ethyl acetate and washed twice with 0.5M sodium hydroxide solution. The organic phase was dried over magnesium sulfate, filtered and concentrated to give the desired product following Kugelrohr distillation; b.p. 75-80° /0.05 mm; yield 20-35%.

Method 2: To a solution of 2 propylpentanal (1 equivalent) and methyl vinyl ketone (1 equivalent) in benzene (400 ml/mol) was added concentrated sulfuric acid (3 ml/mol). The reaction mixture was heated under reflux using a Dean Stark water trap. Reflux was continued for 3-5 hours and no further separation of water was observed. The black reaction mixture was cooled to room temperature and washed with saturated sodium bicarbonate. The organic phase was dried with magnesium sulfate, filtered and concentrated to give a dark brown oil. The oil was kugelrohr distilled to give the desired product as a colorless oil; b.p. 75–85° /0.075 mm; yield 65–75%.

EXAMPLE 4: 4,4-DIPROPYLCYCLOHEXANONE

To a suspension of 10% palladium on carbon (0.1 equivalents) in ethyl acetate was added 4,4 dipropylcyclohex-2-enone, prepared as described in Example 3. The reaction mixture was hydrogenated at 300N/m² hydrogen in a Parr hydrogenation apparatus at room temperature until hydrogen uptake has ceased (0.5–5 hours). The catalyst was removed by filtration through celite and the filtrate was concentrated to give the desired product as a colorless oil. The product was used without further purification. Yield 98%.

EXAMPLE 5: 2 PROPYLPENT 4-ENAL

Toluene, valeraldehyde (1 equivalent) and diisobutylamine (1 equivalent) were combined and heated under reflux using a Dean-Stark water trap. Heating was continued until water ceased to be collected in the trap (1 equivalent of water was collected). The reaction mixture was cooled to room temperature and toluene was removed under reduced pressure. To the colorless residue acetonitrile (500 ml/mol) was added followed by allyl bromide (1.5 equivalents). The reaction mixture was heated at reflux for 16–24 hours.

The reaction mixture was treated with a buffer solution ((acetic acid (60 ml)/sodium acetate (30 g)/water (300 ml))/mol) and heated at reflux for 5 hours. The clear orange brown solution was cooled to room temperature and ethyl acetate (300 ml/mol) and brine (150 ml/mol) were added. The organic phase was subsequently washed with 10% aqueous hydrochloric acid, water, saturated aqueous sodium bicarbonate solution and brine. The organic extract was dried over magnesium sulfate, filtered and concentrated to give a brown oil. The oil was fractionally distilled to give the desired product; b.p. 68–73° /30 mm; yield 50%.

EXAMPLE 6: 2-PROPYLPENTANAL

A Parr hydrogenation bottle was charged with 10% palladium on carbon (0.1 equivalent) and ethyl acetate. A solution of 2-propylpent 4 enal, prepared as in Example 5, in ethyl acetate was added. The mixture was hydrogenated at 300N/m² hydrogen in a Parr hydrogenation apparatus at room temperature until hydrogen uptake ceased. The catalyst was removed by filtration through celite. The filtrate was concentrated to give the desired product as a colorless oil. The product was used without further purification.

SECTION 1A: SYNTHESIS OF 4 SUBSTITUTED CYCLOHEXANONES

The synthesis of 4-decylcyclohexenone is described in Example 7. Similarly other straight chain, branched or cyclic α-substituted aldehydes could be converted into 4 substituted cyclohexanones.

EXAMPLE 7: SYNTHESIS OF 4-DECYLCYCLOHEXANONE

A mixture of potassium carbonate (1 equivalent) and morpholine (3.3 equivalents) were cooled to −5° under an inert atmosphere and dodecanal (1 equivalent) was added dropwise over 30 minutes. The reaction mixture was allowed to warm to room temperature and stirring was continued for 3–6 hours. Addition to ether followed by filtration and concentration gave crude morpholine enamine. The residue was distilled to give the desired product; b.p. 103–108° /0.07 mm; yield 74%.

Under an inert atmosphere the above morpholine enamine (1 equivalent) and methyl vinyl ketone (1.05 equivalents) were combined and stirred overnight at room temperature. A buffer solution ((sodium acetate (70 g)/acetic acid (700 ml)/ethanol (525 ml)/water (175 ml))/mol was added and the solution was heated under reflux for 4–6 hours. The volatile components were removed under reduced pressure and the thick brown oil residue was partitioned between ethyl acetate and water. The organic phase was washed with water and brine, dried over magnesium sulfate, filtered and concentrated to give a light brown viscous oil. The oil was Kugelrohr distilled to give the desired product as a colorless viscous oil; b.p. 122–135° /0.22mm; yield 40%.

The cyclohexenone synthesized above was hydrogenated in a manner similar to that described in Example 6 to give 4-decylcyclohexanone. The product was used without further purification.

Section 2: COMPOUNDS OF FORMULA (I) WHEREIN m IS 1 AND $R_3$ AND $R_4$ ARE OTHER THAN H Scheme 3 outlines the generic synthesis of the azaspirane analogs of Formula (I) wherein m is 1; $R_3$ and $R_4$ are other than H, and n, $R_1$ and $R_2$ are as defined above, startinq from the appropriately substituted cyclohexanones.

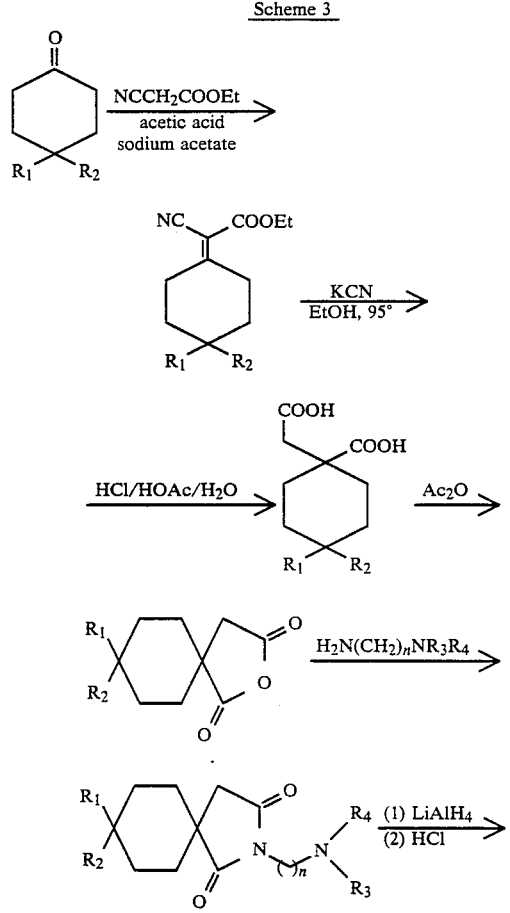

Scheme 3

-continued
Scheme 3

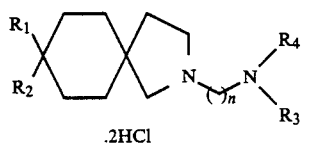

.2HCl

Examples 8-12 below describe the synthesis of 2-(3-dimethylaminopropyl)8,8-diethyl-2-azaspiro[4.5]decane dihydrochloride from 4,4-diethylcyclohexanone. In a similar manner, the following cyclic ketones were reacted to obtain analogous derivatives of compounds of Formula (I) including:
4,4 dipropylcyclohexanone
4,4 dibutylcyclohexanone
4,4 dipentylcyclohexanone
4,4 bis(2-methylpropyl)cyclohexanone
4-ethyl-4 butylcyclohexanone
4 methyl-4 (1 methylpropyl)cyclohexanone
4 cyclohexylcyclohexanone
4 decylcyclohexanone
4 (1,1 dimethylethyl)cyclohexanone Example 11 describes the reaction of an anhydride with dimethylaminopropylamine to give the desired imide. In a similar manner 4,4 dipropylcyclohexane 1-carboxy 1 acetic acid anhydride has been condensed with:
4 dimethylaminobutylamine
5 dimethylaminopentylamine
6 dimethylaminohexylamine
7 dimethylaminoheptylamine
3 diethylaminopropylamine
3 (1 piperidine)propylamine
6 (1 piperidine)hexylamine
3-(1-pyrrolidine)propylamine
6 (1-pyrrolidine)hexylamine
and subsequently reduced as described in Example 12 to give the desired product following hydrochloride formation.

In a similar manner any anhydride derived from the appropriately substituted cyclohexanone may be reacted with any of the above listed amines and subsequently reacted as in Example 12 to give the desired azaspirane analog.

Example 8: Ethyl α-cyano-α-(4,4 diethyl cyclohexylidene)acetate

To a solution of 4,4-diethylcyclohexanone (1 equivalent) in toluene was added ethyl cyanoacetate (1 equivalent), acetic acid (0.2 equivalents) and ammonium acetate (0.1 equivalents). The mixture was heated at reflux employing a Dean Stark apparatus to collect the water azeotropically removed from the reaction. Following collection of one equivalent of water the reaction mixture was cooled and washed with water and saturated aqueous sodium bicarbonate solution. The organic phase was dried over magnesium sulfate, filtered and concentrated. The residue was purified by distillation using a Kugelrohr apparatus to give the desired product as a colorless oil; b.p. 92-98° /0.15mm; yield 80-95%.

Example 9: 4,4 Diethylcyclohexane 1 carboxy-1-acetic acid

To a solution of ethyl α-cyano α-(4,4 diethylcyclohexylidene) acetate (1 equivalent), prepared as described above, in ethanol was added a solution of potassium cyanide (1.15 equivalents) in water. The reaction mixture was heated at 50-85° for 3-9 hours then concentrated to dryness. The residue was treated with hydrochloric acid and extracted with ethyl acetate. The combined organic extracts were dried over magnesium sulfate, filtered and concentrated. The residue was dissolved in a mixture of acetic acid/hydrochloric acid/water ((4.5L/2L/0.21)/mol) and heated at reflux for 2-5 days. The volatiles were removed under reduced pressure and the solid residue was partitioned between water and ethyl acetate. The organic extract was dried with magnesium sulfate, filtered and concentrated to give the desired diacid as a white solid. Recrystallization from ethyl acetate gave a white crystalline solid; m.p. 150-152°, yield 75-85%.

Example 10 4,4-Diethylcyclohexane-1-carboxy-1-acetic acid anhydride 4,4 Diethylcyclohexane 1-carboxy 1 acetic acid (1 equivalent), prepared as described in Example 9, was dissolved in acetic anhydride and refluxed for 1-6 hours. The excess acetic anhydride was removed by distillation under reduced pressure and the residue was recrystallized from hexanes; m.p. 91-93°; 90-95% yield.

NOTE: In the cases in which the substituents on the 4 position of the starting cyclohexanone are not identical the geometric isomeric anhydrides were separated by chromatography on a Waters 500 prep system using hexane/ethyl acetate mixtures as eluant.

Example 11: 2-(3-Dimethylaminopropyl) 8,8-diethyl-2-azaspiro[4.5]decane-1,3-dione To a solution of 4,4 diethylcyclohexane 1-carboxy 1 acetic acid anhydride (1 equivalent) in toluene was added 3-dimethylaminopropylamine (1.05 equivalents) and the reaction mixture was heated at reflux using a Dean-Stark trap. Following collection of water (1 equivalent) in the trap the reaction mixture was cooled to room temperature and the solvent was removed under reduced pressure. The residue was used directly without further purification.

Example 12: 2-(3 Dimethylaminopropyl) 8,8 diethyl-2 azaspiro[4.5]decane dihydrochloride To a mixture of lithium alumin equivalents) in diethyl ether was added dropwise a solution of 2-(3 dimethylaminopropyl) 8,8-diethyl 2 azaspiro[4.5]decane1,3 dione (1 equivalent), prepared as described in Example 11, in diethyl ether. The reaction mixture was stirred for 2-6 hours following completion of addition. The excess hydride was quenched with sodium sulfate decahydrate and the resulting mixture was filtered and the filtrate was concentrated to give the desired amine as a colorless oil; 90-95% yield.

The oil was dissolved in a minimum of anhydrous ethanol and a cooled solution of hydrogen chloride in ethanol was added. On addition of a large volume of ether, a white precipitate formed which was isolated by filtration. The white solid was recrystallized from ethanol; m.p. 298-299° (decomp.); 90% yield.

Section 3: COMPOUNDS OF FORMULA (I) WHEREIN m IS 1 AND R₃ AND R₄ ARE H

Scheme 4 outlines the generic synthesis of the azaspirane analogs of Formula (I) wherein m is 1, $R_3$ and $R_4$ are H. and n, $R_1$ and $R_2$ are as defined above, from the appropriately substituted cyclohexanones.

Scheme 4

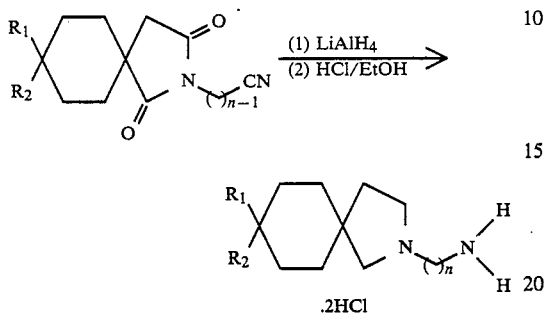

Examples 13 and 14 describes the synthesis of 2-(3 aminopropyl) 8,8 dipropyl 2 azaspiro[4.5]decane dihydrochloride from 4,4 dipropylcyclohexane 1 carboxy 1 acetic acid anhydride.

In a similar manner appropriately substituted cyclohexanones and the anydrides derived therefrom described earlier may be reacted with ω-aminoalkylnitriles (n=4-7) as in Examples 13 and 14 to synthesize the desired azaspiranes wherein $R_3=R_4=H$.

1 EXAMPLE 13: 2 (2 CYANOETHYL) 8,8 DIPROPYL 2 AZASPIRO[4.5]-DECANE 1,3-DIONE

To a solution of 4,4 dipropylcyclohexane-1-carboxy 1 acetic acid anhydride (1 equivalent), prepared analogously to the 4,4-diethyl derivative prepared in Example 10, was added 3-aminopropanenitrile (1.1 equivalents) and toluene. The reaction mixture was heated at reflux using a Dean Stark trap. Following collection of water (1 equivalent), the reaction mixture was cooled to room temperature and the solvent was removed under reduced pressure. The residue was purified by column chromatography (hexane/ethyl acetate (2/1)) to give a white solid; m.p. 117-117.5°; yield 95%.

EXAMPLE 14: 2 (3 AMINOPROPYL) 8,8 DIPROPYL-2 AZADPIRO[4 5]-DECANE DIHYDROCHLORIDE

To a mixture of lithium aluminum hydride (4 equivalents) in diethyl ether was added dropwise a solution to 2 (2 cyanoethyl) 8,8 dipropyl 2 azaspiro[4.5]decane 1,3 -dione (1 equivalent), prepared as described in Example 13, in diethyl ether. The reaction mixture was stirred for 2-4 hours following completion of addition. The excess hydride was guenched with sodium sulfate decahydrate and the resulting mixture was filtered and the filtrate was concentrated. The resulting liquid was purified by preparative liquid chromatography (silica gel; 2.5% ammonium hydroxide in methanol) to give the desired amine as a colorless oil; 73% yield.

The oil was dissolved in a minimum amount of anhydrous ethanol and a solution of hydrogen chloride in ethanol was added. The solution was concentrated to give a white solid; m.p. 245-249° (decomp); 95% yield.

Section 4: COMPOUNDS OF FORMULA (I) WHEREIN m IS 1 AND $R_3$ IS OTHER THAN H AND $R_4$ IS H Scheme 5 outlines the generic synthesis of the azaspirane analogs of Formula (I) wherein m is 1, one of $R_3$ and $R_4$ is H while the other is other than H, and n, $R_1$ and $R_2$ are as defined above, from the appropriately substituted cyclohexanones.

Scheme 5

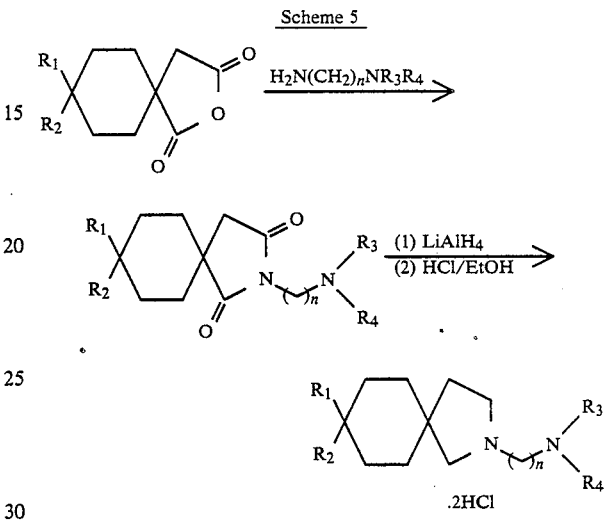

Example 15 and 16 describes the synthesis of (3 methylaminopropyl)-8,8 dipropyl-2 azaspiro[4.5]decane dihydrochloride from 4,4 dipropylcyclohexane 1 carboxy 1 -acetic anhydride.

In a similar manner the appropriately substituted cyclohexanones described earlier and the anhydrides derived therefrom may be reacted as described in Examples and 16 with ω-alkylaminoalkylamines (n=4-8) to give azaspirane derivatives wherein $R_3$=alkyl and $R_4$=H.

EXAMPLE 15: 2 (3 METHYLAMINMOPROPY L 8,8 DIPROPYL-2 AZASPIRO-[4.5]DECANE-1,3-DIONE

To a solution of toluene and 4,4 dipropylcyclohexane 1 carboxy 1 acetic acid anhydride (1 equivalent) was added 3 methylaminopropylamine (1.05 equivalents). The reaction mixture was heated at reflux using a Dean Stark trap. Following collection of water (1 equivalent), the reaction mixture was cooled to room temperature and concentrated under reduced pressure. The residue was used without further purification.

EXAMPLE 16: 2-(3 METHYLAMINOPROPYL)-8,8 DIPROPYL2-AZASPIRO-[4.5]DECANE DIHYDROCHLORIDE

To a mixture of lithium aluminum hydride (4 equivalents) in diethyl ether was added dropwise a solution of 2-(3-methylaminopropyl) 8,8 dipropyl-2 azaspiro [4.5]decane-1,3-dione (1 equivalent), prepared as described in Example 15, in diethyl ether. The reaction was worked up as in Example 14. The product was purified by column chromatography (silica gel; 0.5% ammonium hydroxide in methanol) to give a colorless oil; 67% yield.

The oil was dissolved in a minimum of anhydrous ethanol and a solution of hydrogen chloride in ethanol was added. A white precipitate formed upon cooling which was isolated by filtration; m.p. 258-260° (decomp); yield 84%.

Section 5: COMPOUNDS OF FORMULA (I) WHEREIN m IS 2

Scheme 6 outlines the route to alkyl substituted azaspiro[5.5]undecane analogs starting from the appropriately substituted cyclohexanones.

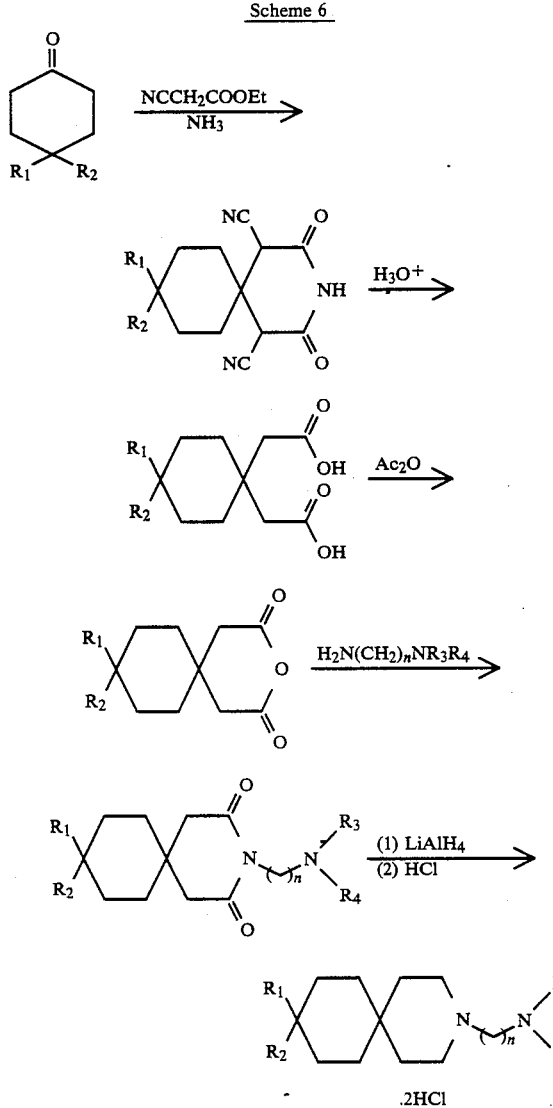

Scheme 6

Examples 17 21 below describe the preparation of (3 dimethylamino)propyl 9,9 dipropyl 3 azaspiro[5.5]undecane dihydrochloride from 4,4 dipropylcyclohexanone.

In a similar manner the appropriately substituted cyclohexanones as described earlier (see Sections 1, 1A and 2) and the anhydrides derived therefrom as described in this Section may be reacted with:

(a) dialkylaminoalkylamines as described in Section of the Synthetic Examples to give azaspirane derivatives wherein $R_3 = R_4 = $ alkyl (b) aminoalkylnitriles as described in Section 3 of the Synthetic Examples to give azaspirane derivatives wherein $R_3 = R_4 = H$ (c) alkylaminoalkylamines as described in Section 4 of the Synthetic Examples to give azaspirane derivatives wherein $R_3 = $ alkyl and $R_4 = H$.

EXAMPLE 17: 9,9 DIPROPYL 1,5 DICYANO 3 AZASPIRO [5.5]-UNDECANE-2,4-DIONE

To a solution of 4.4 dipropylcyclohexanone (1 equivalent) and ethyl cyanoacetate (2 equivalents) in ethanol cooled to 0° was added a saturated alcoholic ammonia solution. The reaction mixture was stoppered and allowed to react a 0° for two to seven days. The precipitated ammonium salt of the dicyanoimide was filtered, pressed, washed with ether and dried. The dried salt was dissolved in a minimum amount of boiling water and filtered hot. The hot filtrate was stirred and acidified with concentrated hydrochloric acid and after cooling the precipitated product was isolated by filtration to yield the desired imide; yield 33%.

EXAMPLE 18: 4,4 DIPROPYLCYCLOHEXANE 1,1-DIACETIC ACID 9,9-Dipropyl-1,5 -dicyano-3 -azaspiro[5.5]undecane-2,4 -dione, prepared according to the method of Example 17, was dissolved in a solution of concentrated hydrochloric acid/acetic acid/water (4/7/1) and the solution was heated at reflux for 2 3 days. The reaction mixture was cooled to room temperature and the volatile materials were removed on the rotavap. The residue was partitioned between water and ethyl acetate. The organic phase was washed with brine, dried over magnesium sulfate, filtered and concentrated to give the desired acid which was recrystallized from ethyl acetate/hexanes; yield 35-50%.

EXAMPLE 19: 4,4 -DIPROPYLCYCLOHEXANE-1,1-DIACETIC ACID ANHYDRIDE 4,4-Dipropylcyclohexane-1,1 diacetic acid, prepared as described in Example 18, was dissolved in acetic anhydride and refluxed for 1-6h. The excess acetic anhydride was removed by distillation under reduced pressure and the residue was recrystallized form hexanes; m.p. 91-93° ; yield 90-95%.

EXAMPLE 20: 3-(3-DIMETHYLAMINOPROPYL-9,9-DIPROPYL-3 AZASPIRO[5.5]UNDECANE-2,4-DIONE

This imide was prepared from 9,9 dipropylcyclohexane 1, 1 diacetic acid anhydride (1 equivalent), prepared as described in Example 19, and 3 dimethylaminopropylamine (1 equivalent) in a similar manner to the described in Example 11. The product, a colorless oil, was used without further purification.

EXAMPLE 21: 3-(3 -DIMETHYLAMINOPROPYL)-9,9-DIPROPYL-3-AZASPIRO[5.5]UNDECANE DIHYDROCHLORIDE

The amine was prepared by lithium aluminum hydride reduction of 3-(dimethylamino)propyl-9,9-dipropyl-3-azaspiro[5.5]undecane -2,4-dione, prepared as described in Example 16, in a manner similar to that described in Example 12. The crude white solid was precipitated by addition of ether and recrystallized from ethanol; m.p. >320° decomp.; yield 85-90%.

Section 6: SYNTHESIS OF POLYCYCLIC AZASPIRANE DERIVATIVES OF FORMULA (II)

2 Adamantanone was converted into a 4,4 spirosubstituted cyclohexanone as described in Section 1 and subsequently converted into the desired azaspirane analog using the methodology described in Section 2 (Examples 8–12); 329–330°.

2-Adamantanone was converted into the desired azaspirane derivative using the methodology described in Section 2 (Examples 8 12); m.p. 300–302°.

2 Adamantanone could also be reacted as described in Section 5 to give azaspirane derivatives wherein m=2.

In a similar manner the anhydride from 2 adamantanone synthesized either as described in Section 2 or Section 5 could be reacted with:

(a) dialkylaminoalkylamines as described in Section 2 of the Synthetic Examples to give azaspirane derivatives wherein $R_3=R_4=$alkyl (b) aminoalkylnitriles as described in Section 3 of the Synthetic Examples to give derivatives wherein $R_3=R_4=H$ (c) alkylaminoalkylamines as described in Section 4 of the Synthetic Examples to give azaspirane derivatives wherein $R_3=$alkyl and $R_4=H$.

Bicyclo[3.3.1]nonan-9 one was similarly reacted as in Section 2 to give the desired azaspirane derivative; m.p. 303–304°. This ketone could also be modified similarly to 2 adamantanone to give similarly substituted diamine derivatives.

3,3 Dimethylbicyclo[3.3.1]nonan-9 one and 3,3,7,7 tetramethylbicyclo[3.3.1]nonan 9-one (prepared according to Y. Chan, Ph.D. Dissertation, University of Utah (1972) could similarly be reacted as described above for the parent system.

The Chan dissertation is a publicly available document and is easily accesible from the U-M-I Dissertation Information Service, 300 N. Zeeb Road, Ann Arbor, Mich. 48106, telephone (800) 521-0600 or (313) 761-4700. In the Chan dissertation, 3,3,7,7-Tetramethylbicyclo(3.3.1)nonan-9-one was synthesized according to the following procedure:

3.3.7.7-Tetramothylbicyclo(3.3.1)nonan-9)-one(1) was synthesized for the conformational study of bicyclo(3.3.1)nonane systems.

Both the title compound 1 and 3,3-dimethylbicyclo(3.3.1)-nonan-9-one were found to be in twist-twin-boat forms at room temperature.

The title compound 1 was prepared in the following way.

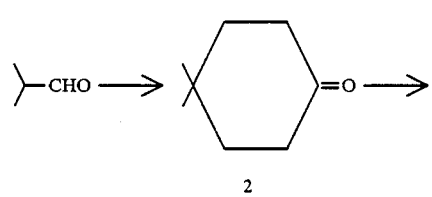

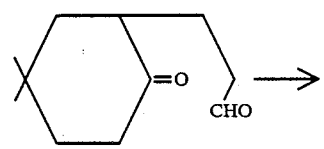

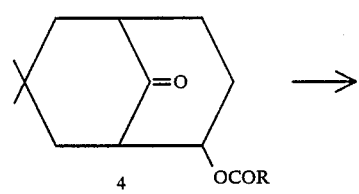

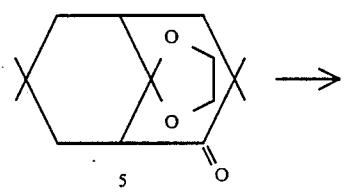

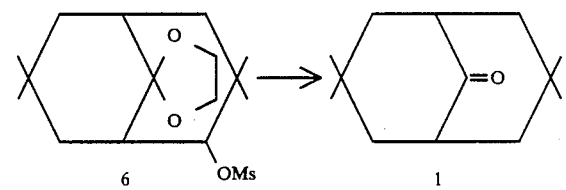

Isobutyraldohyde was alkylated with methyl vinyl ketone via its pyrrolidine enamine, cyclized in acid, and then hydrogenated to give 4,4-dimethylcyclohexanone (2). Ketone 2 was alkylated with acrolein via its morpholline enamine then hydrolyzed to give 3-(2-oxocyclohexyl)propanal (3). Crude 3 was then purified through its diketal, cyclized in 7 N hydrochloric acid, and esterified to give 7,7-dimethylbicyclo(3.3.1)nonan-9-one-2-yl pivalate (4). Kettalization of 4 followed by alkaline hydrolysis, CrO,—pyridine oxidation, and alkylation with iodomethane and potassium t-butoxide yielded 3,3,7,7-tetramothyl-9,9-ethylenedioxybicyclo(3.3.1)nonan2one (5). When various attempts of Wolff-Kishner reduction failed, 5 was reduced to alcohol with lithium—ammonia then mesylated to give 3,3,7,7-tetramethyl-9,9-ethylenedioxybicyclo(3.3.1)nonan-2-exo-yl methanesulfonae (6). Lithium—ammonia reduction of 6 followed by acid hydrolysis afforded the title compound 1.

TABLE 3

Melting Points (decomposition) of Compounds of Formula (I) and Formula (II) Prepared According to the Method of the Synthetic Examples

| #[a] | m.p. (°C.) |
|---|---|
| 01 | 300–302 |
| 02 | 299–300 |
| 03 | 299–301 |
| 04 | 301–302 |
| 05 | 297–298 |
| 06 | 245–249 |
| 07 | 258–260 |
| 08 | 295–296 |
| 09 | 296–298 |
| 10 | 289–291 |
| 11 | 303–304 |
| 12 | 306–307 |

TABLE 3-continued
Melting Points (decomposition) of Compounds
of Formula (I) and Formula (II) Prepared
According to the Method of the Synthetic Examples

| #[a] | m.p. (°C.) |
|---|---|
| 13 | 297–298 |
| 14 | 326–328 |
| 15 | 325–326 |
| 16 | 334–335 |
| 17 | 305–307 |
| 18 | 252–254 |
| 19 | 285–286 |
| 20 | 266–269 |
| 21 | 274–276 |
| 22 | 259–261 |
| 23 | 245–246 |
| 24 | 329–330 |
| 25 | 308–310 |
| 26 | 323–325 |
| 27 | 284–286 |
| 28 | 287–289 |
| 29 | 293–296 |
| 30 | 271–272 |
| 31 | 275–278 |
| 32 | 240–245 |

[a] See Table 1 for structure

TABLE 4
Elemental Analysis of Compounds
of Formula (I) and Formula (II) Prepared
According to the Method of the Synthetic Examples

| # | Molecular Formula | Mol. Wgt. | Calculated for: C: | H: | N: | Cl: | Found: C: | H: | N: | Cl: |
|---|---|---|---|---|---|---|---|---|---|---|
| 01 | $C_{18}H_{38}N_2Cl_2$ | 353.5 | 61.17 | 10.83 | 7.93 | 20.06 | 60.98 | 10.78 | 7.64 | 20.01 |
| 02 | $C_{20}H_{42}N_2Cl_2$ | 381.5 | 62.97 | 11.10 | 7.34 | 18.59 | 62.73 | 10.97 | 7.32 | 18.42 |
| 03 | $C_{22}H_{46}N_2Cl_2$ | 409.5 | 64.52 | 11.32 | 6.84 | 17.31 | 64.69 | 11.34 | 6.82 | |
| 04 | $C_{24}H_{50}N_2Cl_2$ | 437.6 | 65.88 | 11.52 | 6.40 | 16.20 | 66.04 | 11.42 | 6.31 | 16.39 |
| 05 | $C_{22}H_{46}N_2Cl_2$ | 409.5 | 64.52 | 11.32 | 6.84 | 17.31 | 64.23 | 11.32 | 6.76 | 17.28 |
| 06 | $C_{18}H_{38}N_2Cl_2$ | 353.4 | 61.17 | 10.84 | 7.93 | 19.30 | 61.03 | 10.90 | 7.85 | 19.97 |
| 07 | $C_{19}H_{40}N_2Cl_2$ | 367.4 | 62.11 | 10.97 | 7.62 | 19.30 | 62.06 | 10.99 | 7.58 | 19.33 |
| 08 | $C_{21}H_{44}N_2Cl_2$ | 395.5 | 63.78 | 11.21 | 7.08 | 17.93 | 63.68 | 11.07 | 7.08 | 18.12 |
| 09 | $C_{19}H_{40}N_2Cl_2$ | 367.4 | 62.11 | 10.97 | 7.62 | 19.30 | 62.06 | 10.98 | 7.61 | 19.35 |
| 10 | $C_{19}H_{40}N_2Cl_2$ | 367.4 | 62.11 | 10.97 | 7.62 | 19.30 | 61.99 | 11.01 | 7.58 | 19.36 |
| 11 | $C_{20}H_{42}N_2Cl_2$ | 381.5 | 62.97 | 11.10 | 7.34 | 18.59 | 62.92 | 11.11 | 7.30 | 18.64 |
| 12 | $C_{20}H_{42}N_2Cl_2$ | 381.5 | 62.97 | 11.10 | 7.34 | 18.59 | 62.88 | 11.13 | 7.31 | 18.65 |
| 13 | $C_{24}H_{50}N_2Cl_2$ | 437.6 | 65.88 | 11.52 | 6.40 | 16.20 | 65.89 | 11.52 | 6.38 | 16.17 |
| 14 | $C_{20}H_{40}N_2Cl_2$ | 379.5 | 63.31 | 10.62 | 7.38 | 18.69 | 63.24 | 10.64 | 7.37 | 18.68 |
| 15 | $C_{18}H_{38}N_2Cl_2$ | 353.4 | 61.17 | 10.84 | 7.93 | 20.06 | 61.10 | 10.77 | 8.02 | 20.07 |
| 16 | $C_{18}H_{38}N_2Cl_2$ | 353.4 | 61.17 | 10.84 | 7.93 | 20.06 | 61.16 | 10.86 | 7.92 | 19.94 |
| 17 | $C_{20}H_{40}N_2Cl_2$ | 379.5 | 63.31 | 10.62 | 7.38 | 18.69 | 63.22 | 10.67 | 7.35 | 18.70 |
| 18 | $C_{22}H_{46}N_2Cl_2$ | 409.5 | 64.52 | 11.32 | 6.84 | 17.31 | 64.42 | 11.32 | 6.82 | 17.39 |
| 19 | $C_{23}H_{46}N_2Cl_2$ | 421.5 | 65.53 | 11.00 | 6.65 | 16.82 | 65.42 | 11.03 | 6.64 | 16.89 |
| 20 | $C_{21}H_{44}N_2Cl_2$ | 395.5 | 63.78 | 11.21 | 7.08 | 17.93 | 63.64 | 10.99 | 6.96 | |
| 21 | $C_{22}H_{46}N_2Cl_2$ | 409.5 | 64.52 | 11.32 | 6.84 | 17.31 | 64.59 | 11.30 | 6.78 | 17.30 |
| 22 | $C_{23}H_{48}N_2Cl_2$ | 423.6 | 65.22 | 11.42 | 6.61 | 16.74 | 65.05 | 11.29 | 6.57 | |
| 23 | $C_{24}H_{50}N_2Cl_2$ | 437.6 | 65.88 | 11.52 | 6.40 | 16.20 | 65.91 | 11.48 | 6.37 | 16.19 |
| 24 | $C_{23}H_{40}N_2Cl_2$ | 417.5 | 66.17 | 10.14 | 6.71 | 16.98 | 66.21 | 10.16 | 6.67 | 16.94 |
| 25 | $C_{18}H_{34}N_2Cl_2$ | 349.4 | 61.88 | 9.81 | 8.02 | 20.29 | 61.30 | 9.70 | 7.85 | |
| 26 | $C_{17}H_{24}N_2Cl_2$ | 337.4 | 60.52 | 10.16 | 8.30 | 21.02 | 60.55 | 10.12 | 8.31 | |
| 27 | $C_{22}H_{44}N_2Cl_2$ | 407.5 | 64.84 | 10.88 | 6.87 | 17.40 | 64.75 | 10.89 | 6.87 | 17.34 |
| 28 | $C_{25}H_{50}N_2Cl_2$ | 449.6 | 66.79 | 11.21 | 6.23 | 15.77 | 66.68 | 11.31 | 6.30 | 15.67 |
| 29 | $C_{26}H_{52}N_2Cl_2$ | 463.6 | 67.36 | 11.30 | 6.04 | 15.29 | 67.39 | 11.29 | 6.03 | 15.24 |
| 30 | $C_{20}H_{40}N_2Cl_2$ | 379.5 | 63.31 | 10.62 | 7.38 | 18.69 | 63.24 | 10.65 | 7.35 | 18.65 |
| 31 | $C_{21}H_{42}N_2Cl_2$ | 393.5 | 64.10 | 10.76 | 7.12 | 18.02 | 60.01 | 10.81 | 7.10 | 17.93 |
| 32 | $C_{20}H_{42}N_2Cl_2$ | 381.5 | 62.97 | 11.10 | 7.34 | 18.59 | 62.83 | 11.11 | 7.31 | 18.52 |

NOTE:
Compounds 03, 20, 22, 25 and 26 were not analyzed for chloride composition While the above descriptions and examples fully describe the invention and the preferred embodiments thereof, it is understood that the invention is not limited to the particular disclosed embodiments coming within the scope of the following claims.

What is claimed is:

1. A compound of the formula:

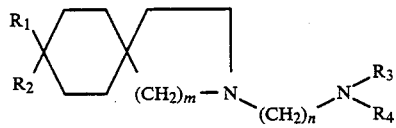

Formula (IA)

wherein:
n is 3–7;
m is 1 or 2;
$R_1$ and $R_2$ are the same or different and are selected from hydrogen or straight chain, branched chain or cyclic alkyl, provided that the total number of carbon atoms contained by $R_1$ and $R_2$ when taken together is 5–10; or $R_1$ and $R_2$ are joined together to form a cyclic alkyl group having 3–7 carbon atoms;
$R_3$ and $R_4$ are the same or different and are selected from hydrogen or straight chain alkyl having 1–3 carbon atoms; or $R_3$ and $R_4$ are joined together to form a cyclic alkyl group having 4–7 carbon atoms;
or a pharmaceutically acceptable salt or hydrate or solvate thereof.

2. The compound of claim 1 which is:

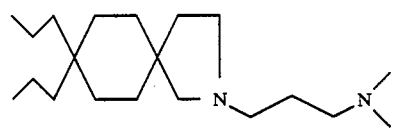

3. The compound of claim 1 which is selected from:
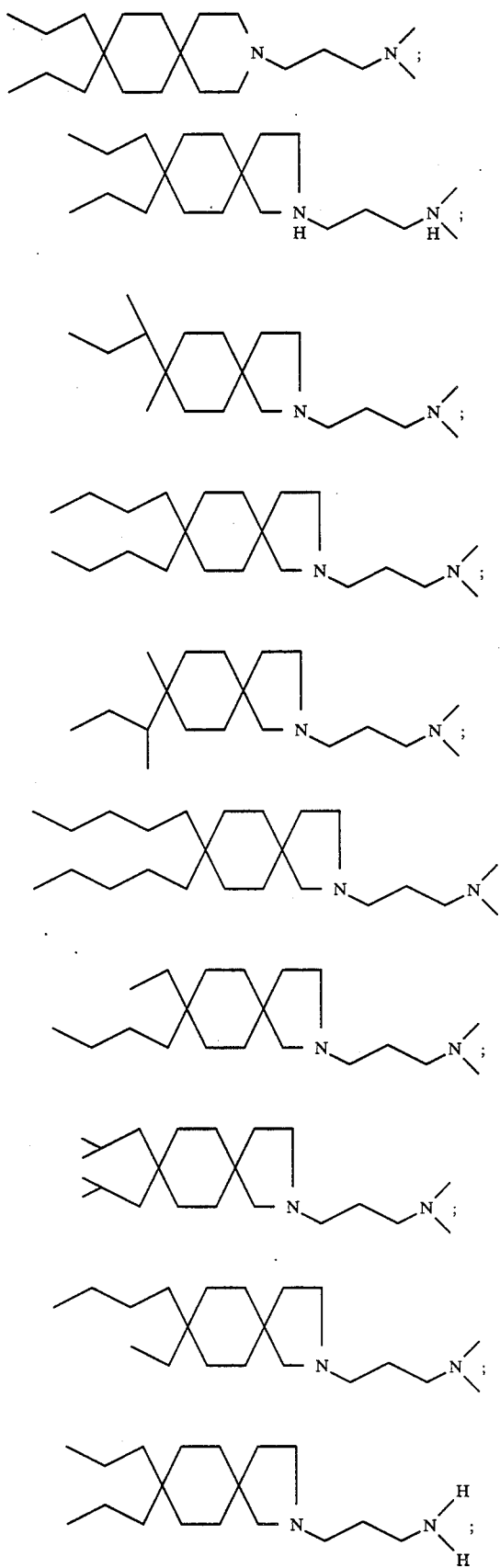
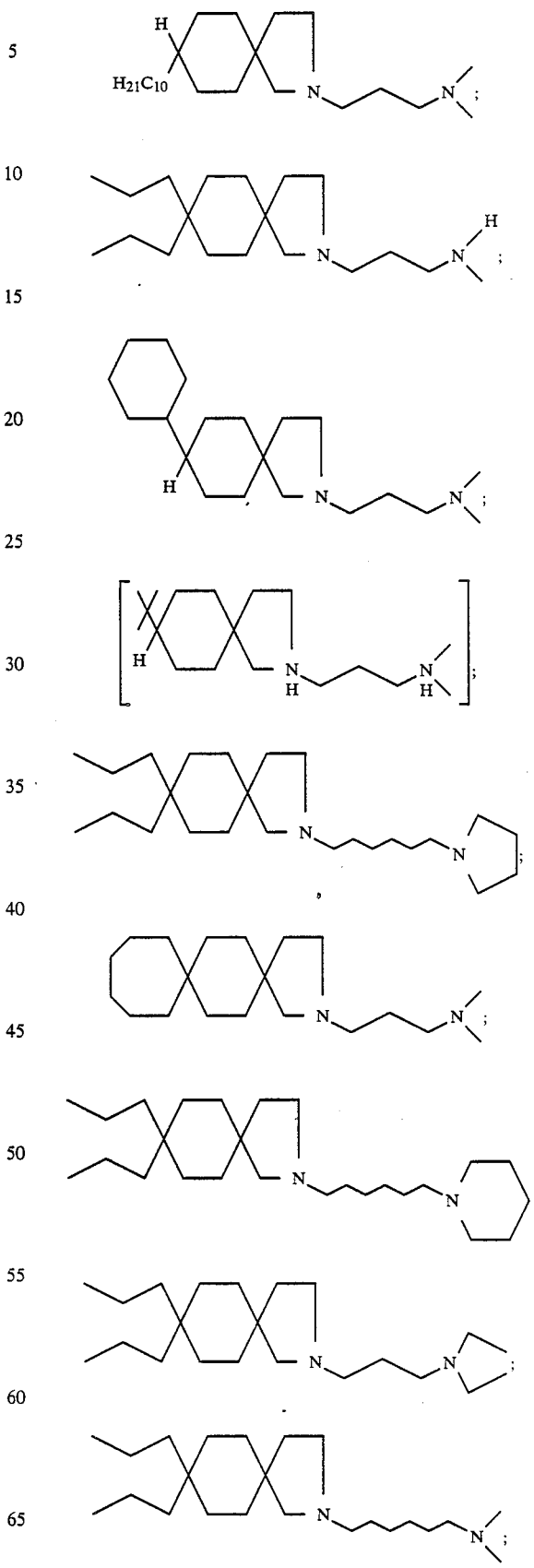

-continued

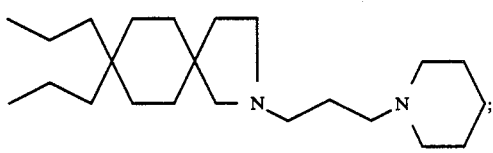

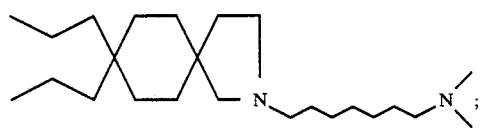

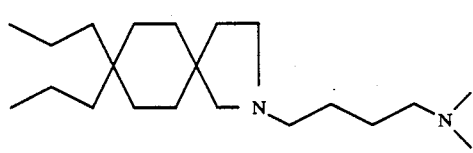

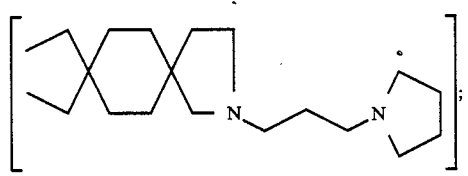

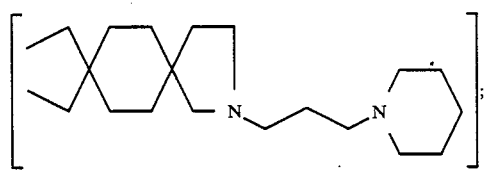

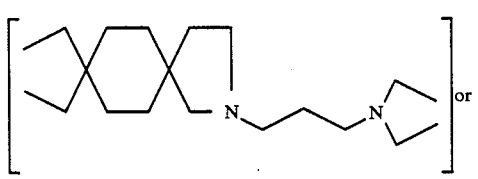

4. A compound of the formula:

Formula (II)

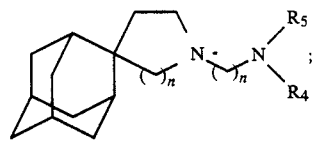

-continued
Formula (II)

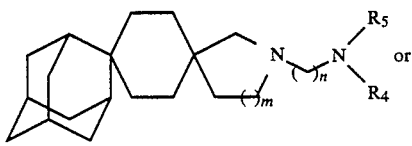

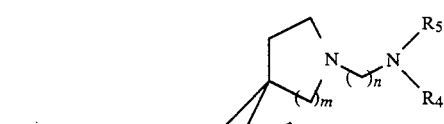

wherein:
n is 3–7;
m is 1 or 2;
$R_1$, $R_2$, $R_5$, and $R_6$ are the same or different and are selected from hydrogen or methyl;
$R_3$ and $R_4$ are the same or different and are selected from hydrogen or straight chain alkyl having (containing) 1–3 carbon atoms; or $R_3$ and $R_4$ are joined together to form a cyclic alkyl group having (containing) 4–7 carbon atoms, or a pharmaceutically acceptable salt, hydrate or solvate thereof.

5. The compound of claim 4 which is selected from:

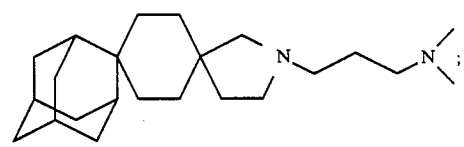

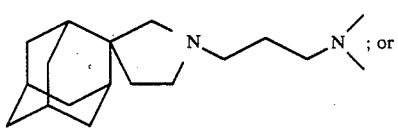

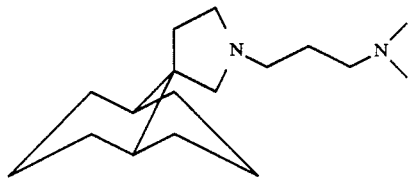

6. A pharmaceutical composition comprising a pharmaceutically acceptable carrier or diluent and an immunomodulatory effective amount of a compound of the formula:

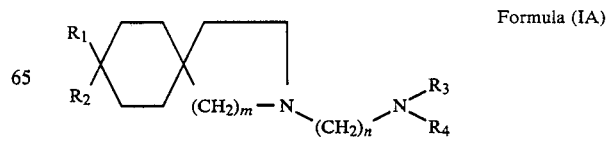

Formula (IA)

wherein:
n is 3–7;
m is 1 or 2;
R₁ and R₂ are the same or different and are selected from hydrogen or straight chain, branched chain or cyclic alkyl, provided that the total number of carbon atoms contained by R₁ and R₂ when taken together is 5–10; or R₁ and R₂ are joined together to form a cyclic alkyl group having 3–7 carbon atoms;
R₃ and R₄ are the same or different and are selected from hydrogen or straight chain alkyl having 1–3 carbon atoms; or R₃ and R₄ are joined together to form a cyclic alkyl group having 4–7 carbon atoms;

or a pharmaceutically acceptable salt or hydrate or solvate thereof.

7. The composition of claim 6 wherein the compound is:

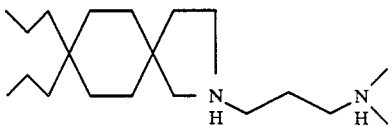

8. The composition of claim 6 wherein the compound is selected from:

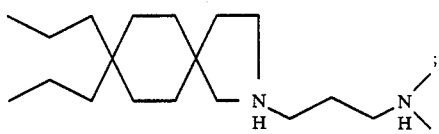

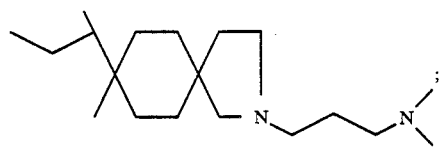

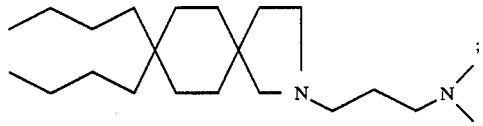

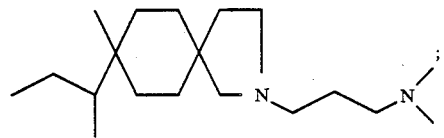

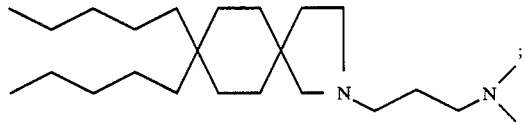

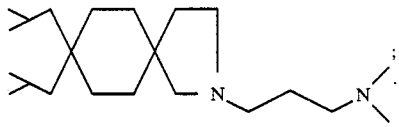

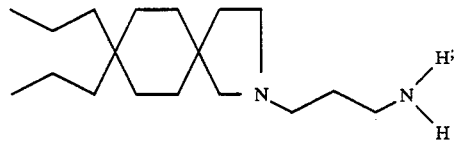

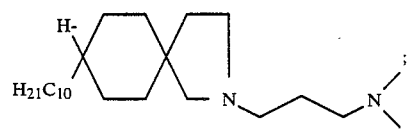

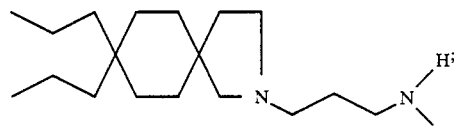

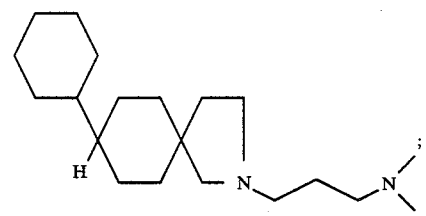

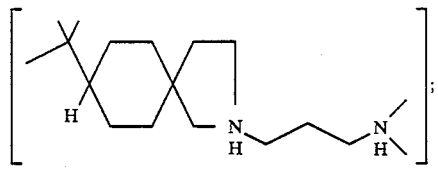

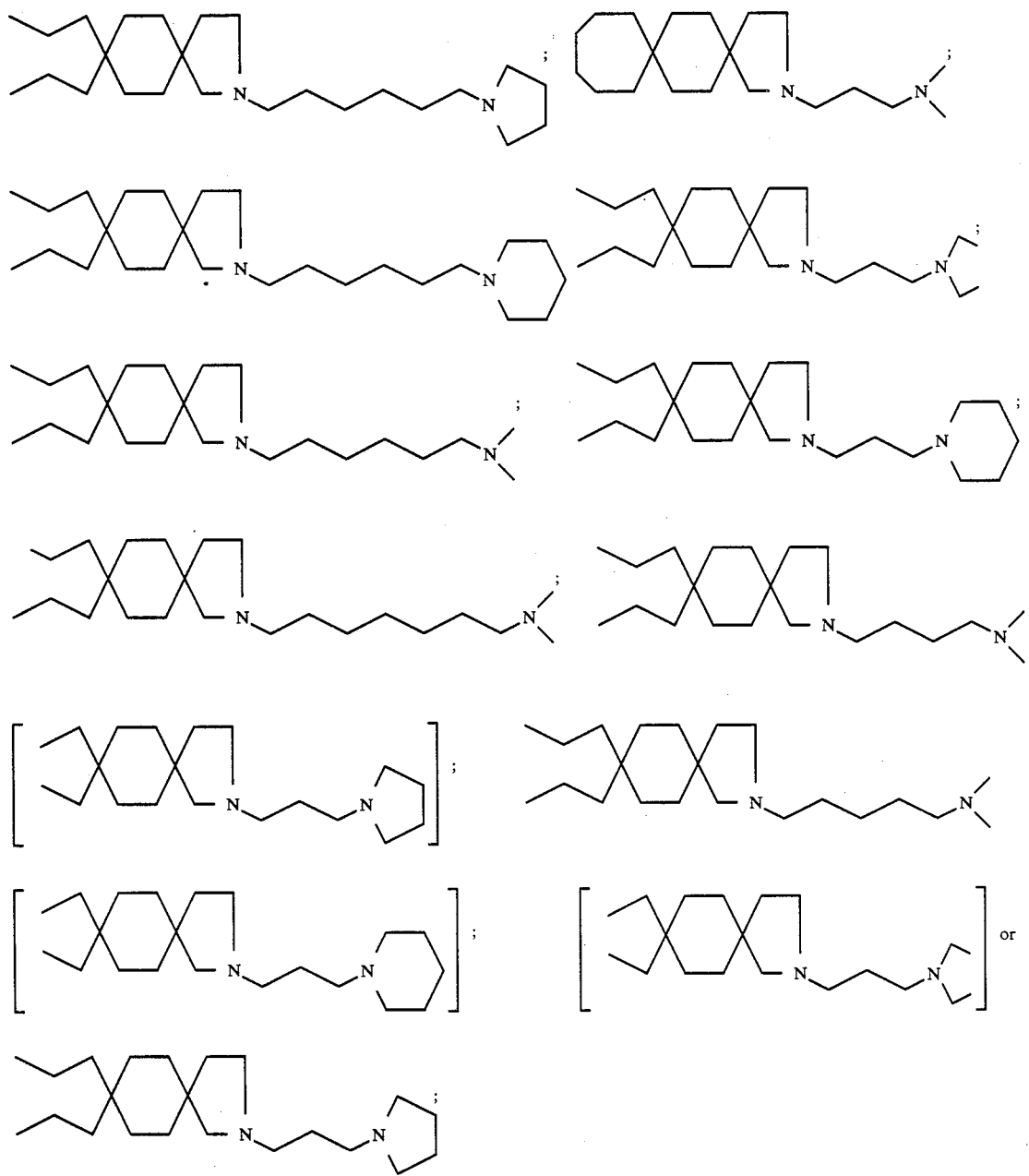

9. The composition of claim 6 which is in a dosage form suitable for oral administration.

10. The composition of claim 6 which is in a dosage form suitable for parenteral administration.

11. The composition of claim 6 which is in a dosage form suitable for administration by inhalation.

12. The composition of claim 6 which is in a dosage form suitable for topical administration.

13. A pharmaceutical composition comprising a pharmaceutically acceptable carrier or diluent and an immunomodulatory effective amount of a compound of the formula:

Formula (II)

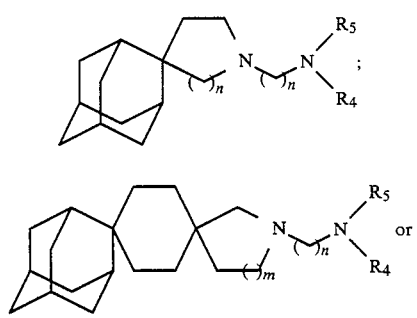

-continued
Formula (II)

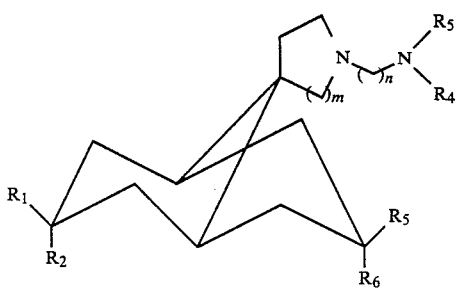

wherein:
n is 3–7;
m is 1 or 2;
R$_1$, R$_2$, R$_5$, and R$_6$ are the same or different and are selected from hydrogen or methyl;
R$_3$ and R$_4$ are the same or different and are selected from hydrogen or straight chain alkyl having (containing) 1–3 carbon atoms; or
R$^3$ and R$_4$ are joined together to form a cyclic alkyl group having (containing) 4–7 carbon atoms, or a pharmaceutically acceptable salt, hydrate or. solvate thereof.

14. The composition of claim 13 wherein the compound is selected from:

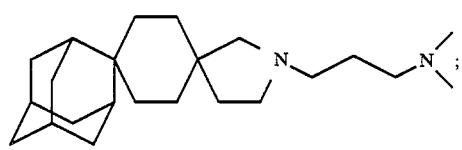

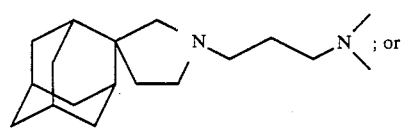

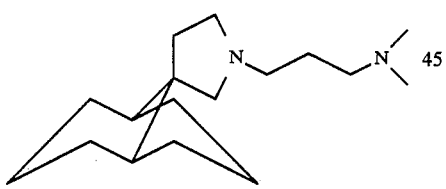

15. The composition of claim 13 which is in a dosage form suitable for oral administration.
16. The composition of claim 13 which is in a dosage form suitable for parenteral administration.
17. The composition of claim 13 which is in a dosage form suitable for administration by inhalation.
18. The composition of claim 13 which is in a dosage form suitable for topical administration.
19. A method of treating an animal in need of immunomodulation which comprises administering to such animal an immunomodulatory effective amount of a compound of the formula:

Formula (I)

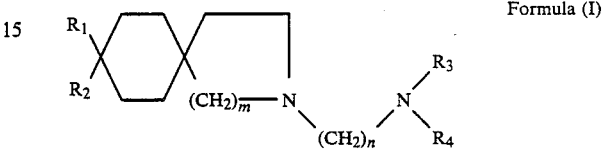

wherein:
n is 3–7;
m is 1 or 2;
R$_1$ and R$_2$ are the same or different and are selected from hydrogen or straight chain, branched chain or cyclic alkyl, provided that the total number of carbon atoms contained by R$_1$ and R$_2$ when taken together is 4–10; or R$_1$ and R$_2$ are joined together to form a cyclic alkyl group having (containing) 3–7 carbon atoms;
R$_3$ and R$_4$ are the same or different and are selected from hydrogen or straight chain alkyl having (containing) 1–3 carbon atoms; or R$^3$ and R$_4$ are joined together to form a cyclic alkyl group having (containing) 4–7 carbon atoms, or a pharmaceutically acceptable salt, hydrate or solvate thereof.

20. The method of claim 19 wherein the compound is:

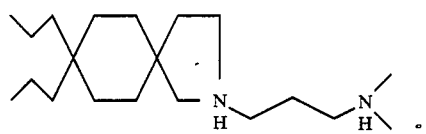

21. The method of claim 12 wherein the compound is selected from:

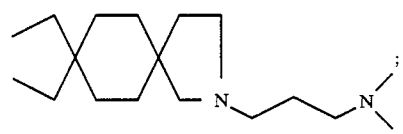

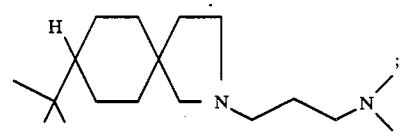

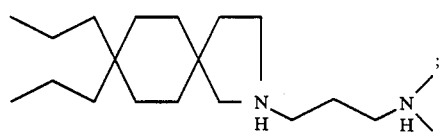

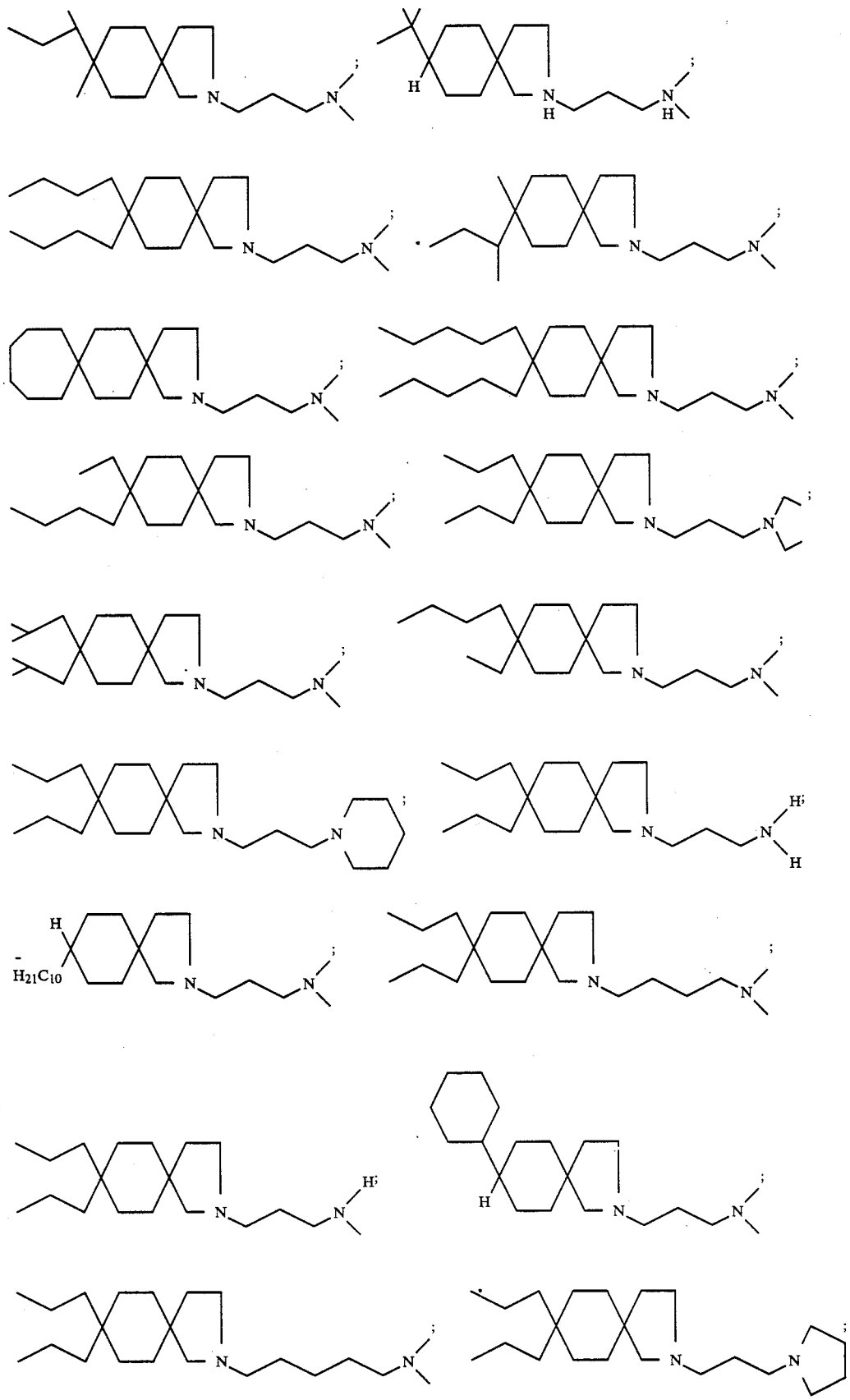

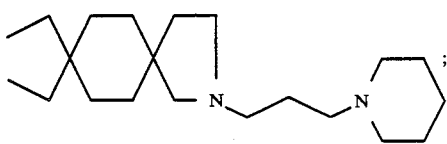

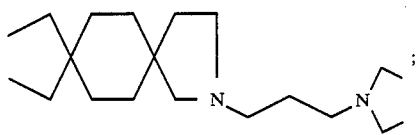

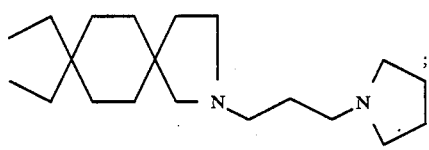

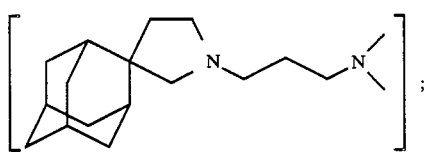

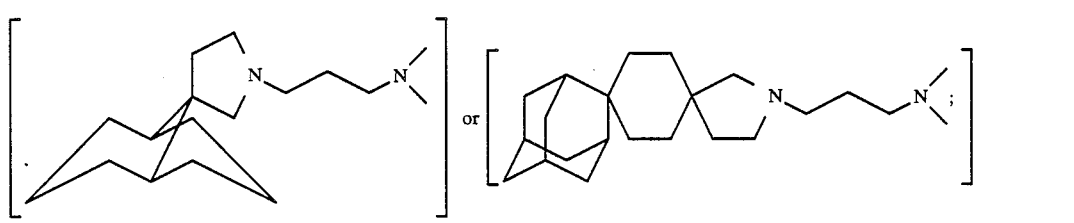

22. The method of claim 19 wherein the compound is administered orally.

23. The method of claim 22 wherein from about 1 to about 2000 mg of compound are administered per day.

24. The method of claim 19 wherein the compound is administered parenterally.

25. The method of claim 24 wherein from about 0.1 to about 1000 mg of compound are administered per day.

26. The method of claim 19 wherein the compound is administered by inhalation.

27. The method of claim 26 wherein from about 10 to about 100 mg of compound are administered per day.

28. The method of claim 19 wherein the compound is administered topically.

29. The method of claim 28 wherein from about 1.5 mg/kg to about 500 mg/kg of body weight are administered per day.

30. A method of treating an animal in need of immunomodulation which comprises administering to such animal an immunomodulatory effective amount of a compound of the formula:

Formula (II)

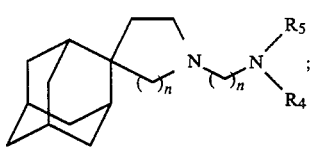

-continued
Formula (II)

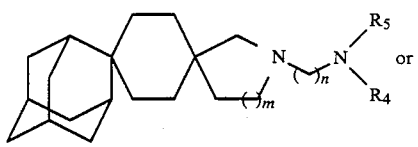

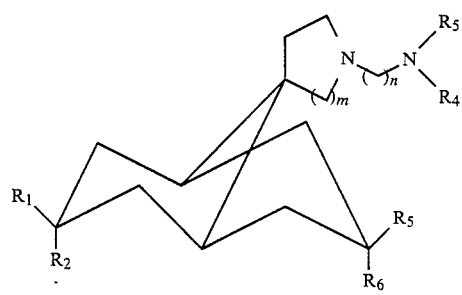

wherein:
 n is 3–7;
 m is 1 or 2;
 $R_1$, $R_2$, $R_5$, and $R_6$ are the same or different and are selected from hydrogen or methyl;

R₃ and R₄ are the same or different and are selected from hydrogen or straight chain alkyl having (containing) 1-3 carbon atoms; or R³ and R₄ are joined together to form a cyclic alkyl group having (containing) 4-14 7 carbon atoms, or a pharmaceutically acceptable salt, hydrate or solvate thereof.

31. The method of claim 30 wherein the compound is selected from:

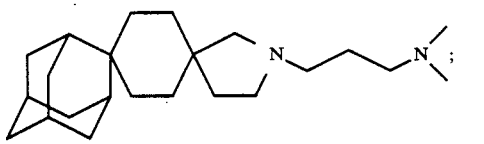

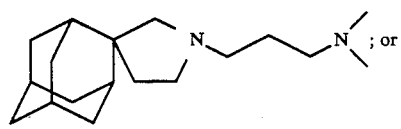 ; or

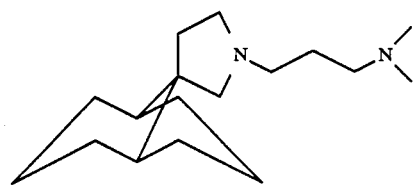

32. The method of claim 30 wherein the compound is administered orally.

33. The method of claim 32 wherein from about 1 to about 2000 mg of compound are administered per day.

34. The method of claim 30 wherein the compound is administered parenterally.

35. The method of claim 34 wherein from about 0.1 to about 1000 mg of compound are administered per day.

36. The method of claim 30 wherein the compound is administered by inhalation.

37. The method of claim 36 wherein from about 10 to about 100 mg of compound are administered per day.

38. The method of claim 30 wherein the compound is administered topically.

39. The method of claim 38 wherein from about 1.5 mg/kg to about 500 mg/kg of body weight are administered per day.

* * * * *